(12) United States Patent
Mitsumori

(10) Patent No.: US 6,409,658 B1
(45) Date of Patent: Jun. 25, 2002

(54) ENDOSCOPE WITH OBJECTIVE LENS DRIVE MECHANISM

(75) Inventor: Naotake Mitsumori, Omiya (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/460,440

(22) Filed: Dec. 14, 1999

(30) Foreign Application Priority Data

| Dec. 14, 1998 | (JP) | 10-354722 |
| Dec. 24, 1998 | (JP) | 10-366224 |
| Jan. 11, 1999 | (JP) | 11-004396 |
| Jan. 11, 1999 | (JP) | 11-004397 |
| Jan. 22, 1999 | (JP) | 11-014133 |
| Sep. 30, 1999 | (JP) | 11-278192 |

(51) Int. Cl.$^7$ ................................ A61B 1/04
(52) U.S. Cl. ........................... 600/167; 600/130
(58) Field of Search ..................... 600/109, 129, 600/130, 167, 160; 348/65, 76; 74/89.37; 359/823

(56) References Cited

U.S. PATENT DOCUMENTS

| 3,434,775 A | * | 3/1969 | Gosselin | 600/167 |
| 4,646,723 A | * | 3/1987 | Arakawa | 600/129 |
| 4,651,718 A | * | 3/1987 | Collins et al. | 600/142 |
| 4,777,524 A | * | 10/1988 | Nakajima et al. | 600/167 |
| 5,255,882 A | * | 10/1993 | Schroppel | 74/89.37 |

FOREIGN PATENT DOCUMENTS

| EP | 0420057 A1 | * | 9/1990 | A61B/1/00 |
| JP | 55-55041 Y2 | * | 12/1980 | A61B/1/00 |

* cited by examiner

Primary Examiner—John Mulcahy
(74) Attorney, Agent, or Firm—Oblon, Spivak, McClelland, Maier & Neustadt, P.C.

(57) ABSTRACT

An endoscope with an objective lens drive mechanism for an objective lens system which is mounted within a rigid tip end section of an insertion instrument of the endoscope. The objective lens system includes a fixed lens which is mounted on a fixed lens frame, and at least one movable lens which is mounted on a movable lens frame. The movable lens frame is slidable along guide surfaces which are provided on the inner periphery of the fixed lens frame in the direction of optical axis of the lens system. A nut portion, which is projected from the movable lens frame substantially in a direction perpendicular to the optical axis, is held in threaded engagement with a screw rod member which is rotatably supported on a bearing member which is in turn supported on the fixed lens frame. The screw rod member is rotatable but blocked against movements in the axial direction. Further, the screw rod is connected with a flexible transmission shaft which is sheathed in a sleeve to transmit rotation to the screw rod. A control cable of the objective lens drive is constituted by the flexible transmission shaft and the sleeve.

14 Claims, 15 Drawing Sheets

F I G. 9
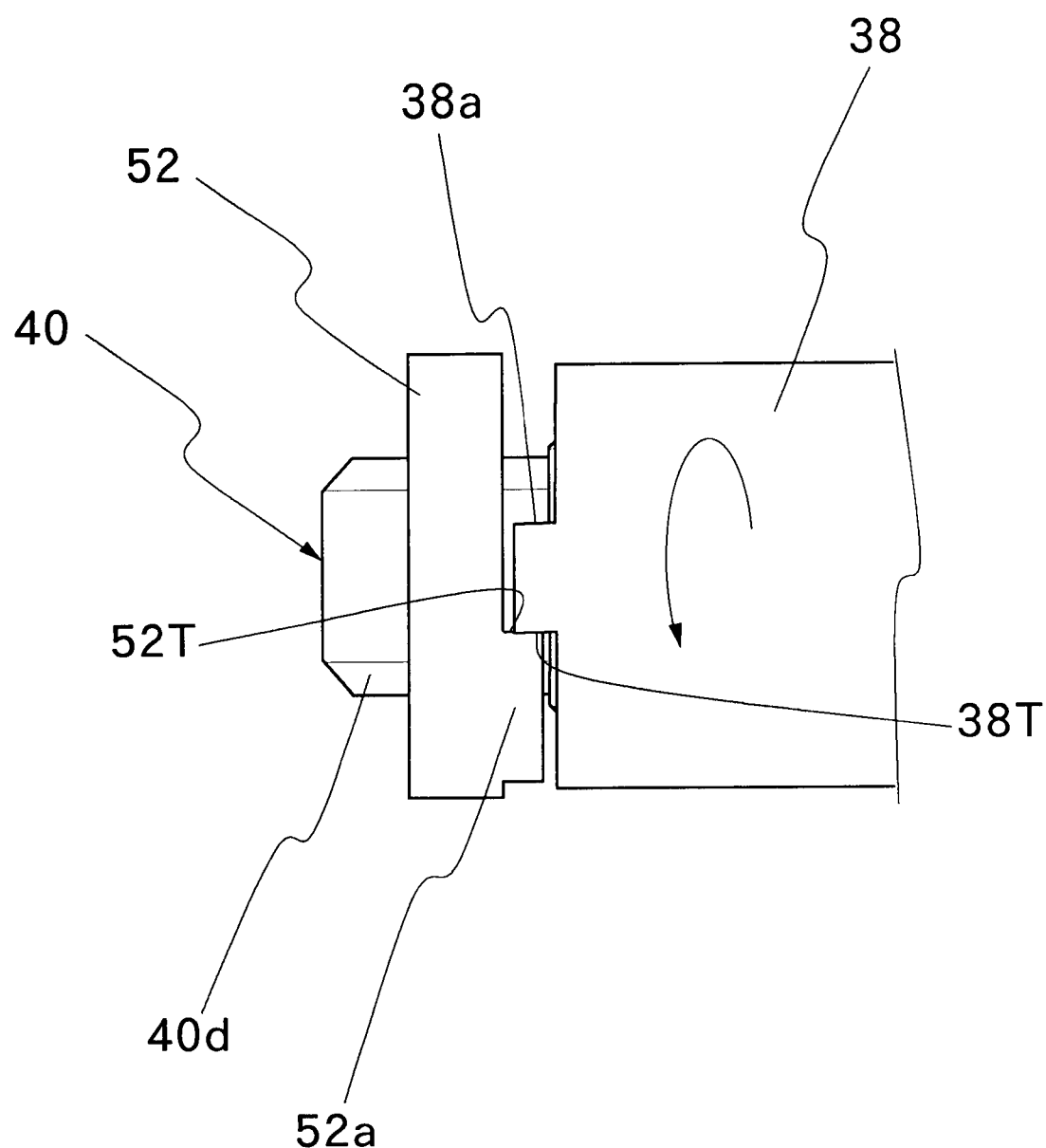

ENDOSCOPE WITH OBJECTIVE LENS DRIVE MECHANISM

BACKGROUND OF THE INVENTION

1. Field of the Art

This invention relates to an endoscope for medical use, incorporating an objective lens drive mechanism in association with an optical objective lens system on its insertion instrument, and more particularly to an endoscope with an objective lens drive mechanism permitting to shift the position of at least one lens element of an optical objective lens system in the direction of its optical axis by remote control to vary at least observation depth, image magnification scale or view field angle.

2. Prior Art

In general, endoscopes which are used for medical purposes are largely constituted by a manipulating head assembly to be gripped by an operator to control the operation of the endoscope, an insertion instrument extended out on the front side of the manipulating head assembly for insertion into a body cavity, and a universal cable led out from the manipulating head assembly for connection to a light source. In terms of construction and function, the insertion instrument is composed of a rigid tip end section, an angle section and a flexible rod section, from its fore distal end to proximal end. The flexible rod section, which occupies a major portion of the entire length of the insertion instrument, is arranged to be flexible in arbitrary directions along a path of insertion which may contain bends. The rigid tip end section is provided with at least an illumination window and an observation window, along with an outlet opening of a biopsy instrument channel which is usually provided in the insertion instrument for the purpose of insertion of forceps or other instruments. The angle section is flexible by remote control from the side of the manipulating head assembly. Accordingly, the rigid tip end section can be turned into an arbitrary direction by bending the angle section by remote control.

A light emitting end of a light guide, which consists of a bundle of fiber optics, is disposed in the illumination window on the rigid tip end section of the insertion instrument. The light guide is passed through the insertion instrument and assembled into the universal cable which is led out from the manipulating head assembly as mentioned above. Further, an objective lens system is mounted on an image pickup assembly block within the rigid tip end section of the insertion instrument, along with a solid-state image sensor device which is located at the focus of the objective lens system. Normally, the image pickup assembly block is located substantially at a central position in a cross-sectional area of the rigid tip end section. On the other hand, it is usually the case that an illumination window is provided at one or a plural number of positions in the vicinity of an observation window at the distal end of the image pickup assembly block. Accordingly, the center of observation view field is located substantially at a central position of the insertion instrument, and the illumination window or windows are arranged to irradiate the entire view field including center portions thereof.

The optical objective lens system of the endoscopic image pickup is normally constituted by an objective lens group which is composed of a plural number of lens elements. Preferably, the objective lens group should be able to vary at least the depth of focus, image magnification rate or view field angle depending upon the location of an observation site or the purpose of examination. In this regard, it has thus far been known in the art to arrange one or a plural number of lens elements of an objective lens group to be movable in the direction of optical axis of the objective lens system. For this purpose, an objective lens group is usually mounted on a lens frame which is constituted by a fixed lens frame and a movable lens frame. The movable lens frame is slidably fitted in the fixed lens frame which functions as a guide when the movable lens frame is moved in the direction of optical axis.

Accordingly, the optical objective lens system necessarily includes a drive means for moving the movable lens frame in the direction of optical axis. As for drive means of this sort, for example, there have been proposed a diversity of drives using piezoelectric elements, shape memory alloys, artificial muscle and the like. However, normally a proximal end of a control cable which is connected to a movable lens frame is extended into the manipulating head assembly of the endoscope thereby permitting to shift the position of a movable lens or lenses in the direction of the optical axis by remote control. The movable lens is moved between a fore position closer to the subject side and a rear position closer to the imaging side. Location of the movable lens in the rear position gives a smaller image magnification rate and a greater focal depth. On the other hand, location of the movable lens in the fore position gives a greater image magnification rate and a smaller focal depth. Accordingly, in this case, the operator can shift the position of the movable lens by driving same through the control cable or other suitable transmission member, depending upon the location of an intracavitary portion under examination or the nature of examination. This shift of the movable lens position is feasible even when the insertion instrument of the endoscope is inserted in a body cavity of a patient.

In order to pick up clear images through an optical objective lens system, a movable lens has to be located precisely in either one of the above-mentioned fore and rear positions. This is so especially when a movable lens is located in a fore position on the side of a subject because the focal depth is shallow in the fore position and therefore a slight deviation from a predetermined position will invite considerable deteriorations in quality of picture images. It follows that a movable lens should be positioned correctly at least when shifted to a fore position on the side of a subject. For remote-controlling a movable lens, a control cable is connected to a movable lens frame as mentioned above. Various forms of remote control cables of this sort have been known in the art, for example, from Japanese Laid-Open Patent Specification H4-13112 and Japanese Utility Model Publication S55-55041.

Disclosed in Japanese Laid-Open Patent Specification H4-13112 is a lens group consisting of a front group lens, a rear group lens and a magnification control lens which is movable in the direction of optical axis. The magnification control lens is arranged to slide along a slide member which is provided between front and rear lens frame which support the front and rear lens groups, respectively. The magnification control lens itself is fitted in a magnification lens frame, and an operating wire is connected to the magnification lens frame thereby to permit to move the latter back and forth by remote control from the manipulating head assembly. The operating wire is passed through and fixedly connected at its fore end to a wire threading member which is provided integrally with the rear group lens frame. The other end of the operating wire is connected to a solenoid which is energizable to shift the magnification control lens between a fore position on the side of the front group lens and a rear position on the side of the rear group lens. The control cable of this sort can be referred to as a push-pull type.

Disclosed in Japanese Utility Model Publication S55-55041 is an endoscope employing an image guide in such a way as to vary the distance between a light incident or input end of the light guide and an optical objective lens system. In this particular prior art, the image guide is moved by the use of a control cable. More particularly, in this case, a projection is provided on a mouth piece which is fitted around a fore end portion of an image guide, and a screw shaft threaded into the projection to connect thereto one end of a wire which is passed through a coil tube. In this case, the position of the light input end of the image guide is adjusted by rotating the wire about the longitudinal axis within the coil tube. The control cable of this sort can be referred to as a rotating type.

Of the above-mentioned two types of control cables, the push-pull type can produce a sufficient driving force through the operating wire when the wire is pulled but not when the wire is pushed. Therefore, it becomes necessary to provide a biasing means at the fore end of the operating wire for biasing the multiplication control lens toward the front group lens. The control cable of this type has another problem that, after repeated operations, the operating wire can get elongated to cause variations in pulling stroke length. On the other hand, the rotating type control cable also has inherent drawbacks that its wire easily gets twisted and fails to transmit rotation smoothly to its fore end, and, gets elongated after repeated use similarly to the above-mentioned push-pull type.

SUMMARY OF THE INVENTION

In view of the foregoing situations, it is an object of the present invention to provide an endoscope with an objective lens drive mechanism which makes it possible to vary at least the depth of observation, image magnification rate or view field angle of an optical objective lens system.

It is another object of the present invention to provide an endoscope with an objective lens drive mechanism which can transmit driving force securely to a movable lens of an objective lens system in reciprocating the movable lens accurately between predetermined positions and which can be operated constantly in stable conditions.

It is still another and more particular object of the present invention to provide an endoscope with an objective lens drive mechanism which can drive a movable lens of an objective lens system accurately relative to a fixed lens of an objective in alignment with optical axis at least to and from a fore position on the side of a subject and a rear position on the side of an imaging plane.

According to the present invention, in order to achieve the above-stated objectives, there is provided an endoscope with an objective lens drive mechanism which comprises: an optical objective lens system incorporated into a rigid tip end section of an insertion instrument of the endoscope and having a fixed lens mounted on a fixed lens frame provided within the rigid tip end section and a movable lens mounted on a movable lens frame for sliding movement in a direction toward and away from the fixed lens along inner surfaces of the fixed lens frame; guide surfaces formed on inner periphery of said fixed lens frame for guiding sliding movements of the movable lens frame in alignment with optical axis of the objective lens system; a nut portion extended out from the movable lens frame in a radially outward direction substantially perpendicularly to said optical axis of said object lens system; a screw rod extended parallel with the optical axis and held in threaded engagement with the nut portion; a bearing member provided on the fixed lens frame and adapted to support the screw rod rotatably relative to the fixed lens frame but to block movements of the screw rod in an axial direction; and a control cable including a flexible transmission shaft connected between the screw rod and a rotational drive means to transmit rotation from the rotational drive means to the screw rod, and sheathed in a fixed sleeve having a fore end thereof securely fixed to the bearing member.

Regarding the arrangements of the objective lens system and movable lens drive means, in one preferred form of the present invention, a prism securely bonded to the fixed lens frame thereby to turn a light path through 90 degrees toward a light receiving surface of a solid-state image sensor device which is located at the focus of the optical objective lens system substantially in parallel relation with a direction in which the control cable is extended. Regarding the location of the solid-state image sensor device, it is preferable to locate the solid-state image sensor device to a radially opposite side of the optical objective lens system within the rigid tip end section away from the direction of radial extension of the nut portion from the movable lens frame. Alternatively, the solid-state image sensor device may be located in a position intermediate between the movable lens frame and the nut portion.

The movable lens should be located accurately in a predetermined position at least on the side of the subject. For this purpose, preferably the screw rod is provided with a stopper mechanism in associated with the nut portion of said movable lens frame, thereby to stop the movable lens frame at least at a preadjusted stroke end position on the side of the subject. In a more particular form of the present invention, the screw rod is provided with a second screw portion in a fore end portion thereof, and the stopper mechanism is provided with a stopper ring in threaded engagement with the second screw portion of the screw rod in such a way that the position of the stopper ring on the second screw portion can be adjusted to preset the nut portion exactly in a stroke end position of the movable lens on the side of a subject. Preferably, the stopper ring and the nut portion are provided with axially projecting sectoral land portions opposingly on confronting end faces, such that the opposing sectoral land portions are brought into abutting engagement with each other at a predetermined stroke end position of the movable lens. Preferably, the stopper mechanism on the screw rod is arranged to stop the movable lens in both a front stroke end position on the side of a subject and a rear stroke end position on the imaging side of the objective lens system.

In order to let the movable lens frame move smoothly when driven through the control cable, preferably the movable lens frame is provided with a sliding surface at two different positions on the circumference thereof, for sliding contact with inner surfaces of the fixed lens frame. Besides, to lessen frictions between the sleeve and the flexible transmission shaft of the control cable, it is preferred to employ for the sleeve a tube which is treated with a lubricant, for example, a silicon rubber tube which is impregnated with silicon oil.

The nut portion is provided at an outer distal end of an arm portion which is connected to and extended out from the movable lens frame, and has a thickness which is substantially same as axial length of the movable lens frame. Preferably, the arm portion is fitted in and extended through an axial slot which is provided in the fixed lens frame, and thereby blocked against rotational movements relative to the fixed lens frame to preclude the possibilities of positional deviations of the movable lens relative to the fixed lens in the rotational direction. In this connection, the nut portion is preferably provided with an axial extension toward a proximal side of the arm portion thereby to increase a length of threaded engagement with said screw rod. In this case, the bearing member on the side of the fixed lens frame is provided with an open receptacle portion of a diameter larger than outside diameter of the nut portion to receive the axial extension of said nut portion therein.

Further, in a preferred form of the present invention, the rigid tip end section of the insertion instrument is connected to a fore end of an angle section of the endoscopic insertion instrument and has an illumination means and a biopsy instrument channel incorporated thereinto in addition to the optical objective lens system, and a pair of operating wires, more preferably, two pairs of operating wires are connected to the angle section for bending same vertically in upward and downward directions and laterally in rightward and leftward directions. In case the fixed lens frame of the optical objective lens system is located substantially at the center of the rigid tip end section of the endoscopic insertion instrument, it is preferred to connect the movable lens frame and the nut portion by way of an arm portion, and to locate the arm portion in an offset position within the rigid tip end section, shifted by a predetermined angle to the right or left of a center line of upward and downward being motions of the angle section, and to locate the control cable and the biopsy instrument channel on the opposite sides of the center line of bending motions of the angle section. The arrangement makes it possible to bend the angle section smoothly in a reliable manner. Further, in a sectional area of the angle section taken perpendicularly to a longitudinal axis thereof and divided into four subdivisions by two perpendicularly intersecting lines drawn between said first and second pairs of operating wires, it is preferred to locate at least the biopsy instrument channel solely in one of the subdivisions, the control cable in another subdivision along with other internally threaded component parts of the insertion instrument in such a way as to keep balance with the biopsy instrument channel in stiffness in bending directions, and other internally threaded components of the insertion instrument in other subdivisions of the angle section.

The above and other objects, features and advantages of the present invention will become apparent from the following particular description, taken in conjunction with the accompanying drawings which show by way of example some preferred embodiments of the present invention.

BRIEF DESCRIPTION OF THE DRAWINGS

In the accompanying drawings:

FIG. 9 is a schematic illustration explanatory of conditions of the nut portion and stopper ring in fitting engagement with each other.

DESCRIPTION OF PREFERRED EMBODIMENTS

Hereafter, the present invention is described more particularly by way of its preferred embodiments. In the following description, the present invention is illustrated by way of an electronic endoscope employing a solid-state image sensor and an optical objective lens system incorporating a prism to bend an optical axis at right angles or through 90 degrees. However, it is to be understood that the present invention can be similarly applied to optical endoscopes having an image guide located at the focus of an objective lens system or to other electronic endoscopes having no prism in an objective lens system.

Figure 1:
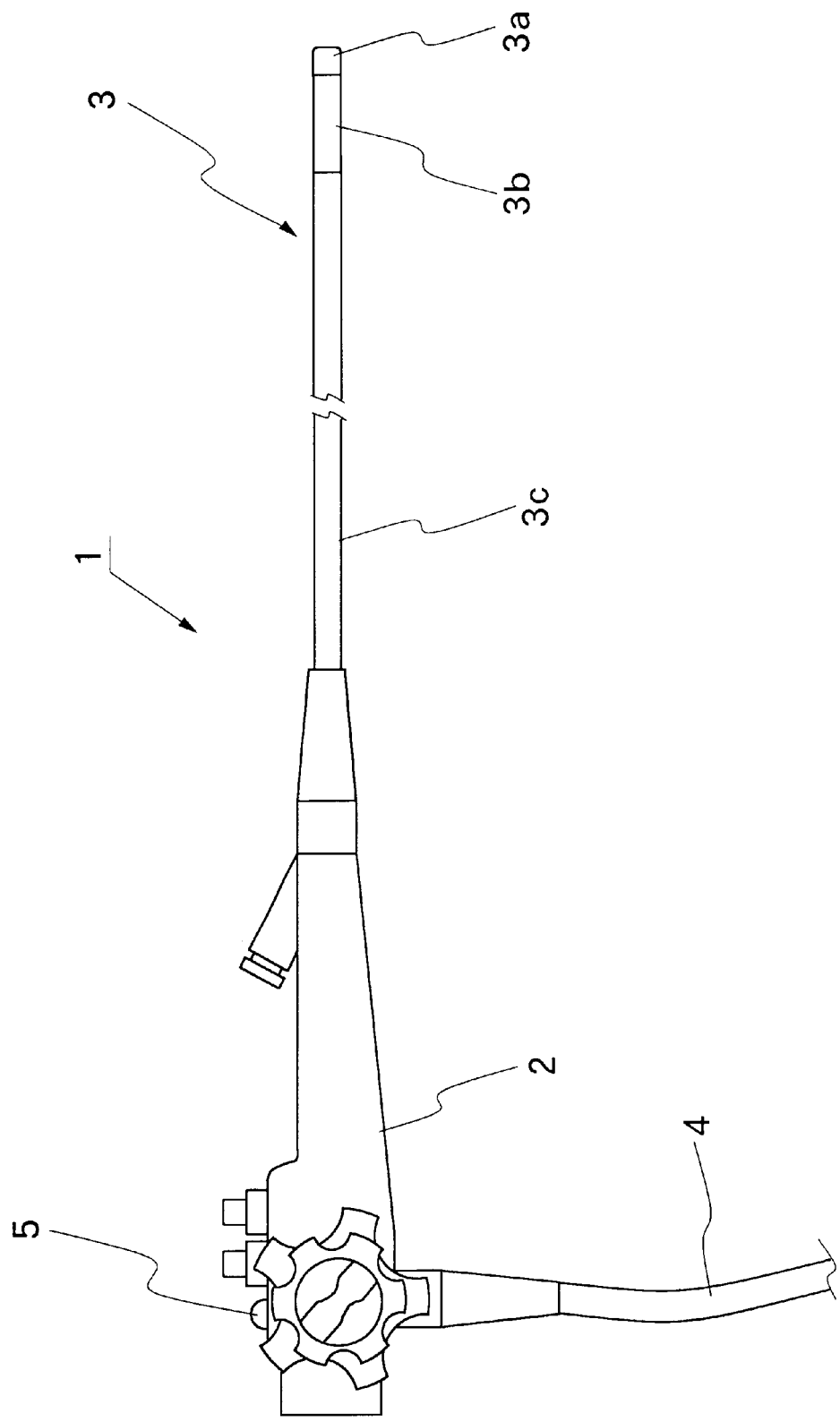
FIG. 1 is a schematic view of an endoscope incorporating a first embodiment of the present invention.

Shown schematically in FIG. 1 is a layout of an endoscope as a whole. As seen in that figure, an endoscope 1 is largely constituted by a manipulating head assembly 2, an insertion instrument 3 which is extended out on the front side of the manipulating head assembly 2, and a universal cable 4 which is led out from the manipulating head assembly 2. The insertion instrument is comprised of, from its fore to distal end, a rigid tip end section 3a, an angle section 3b and a flexible rod section 3c.

Figure 2:
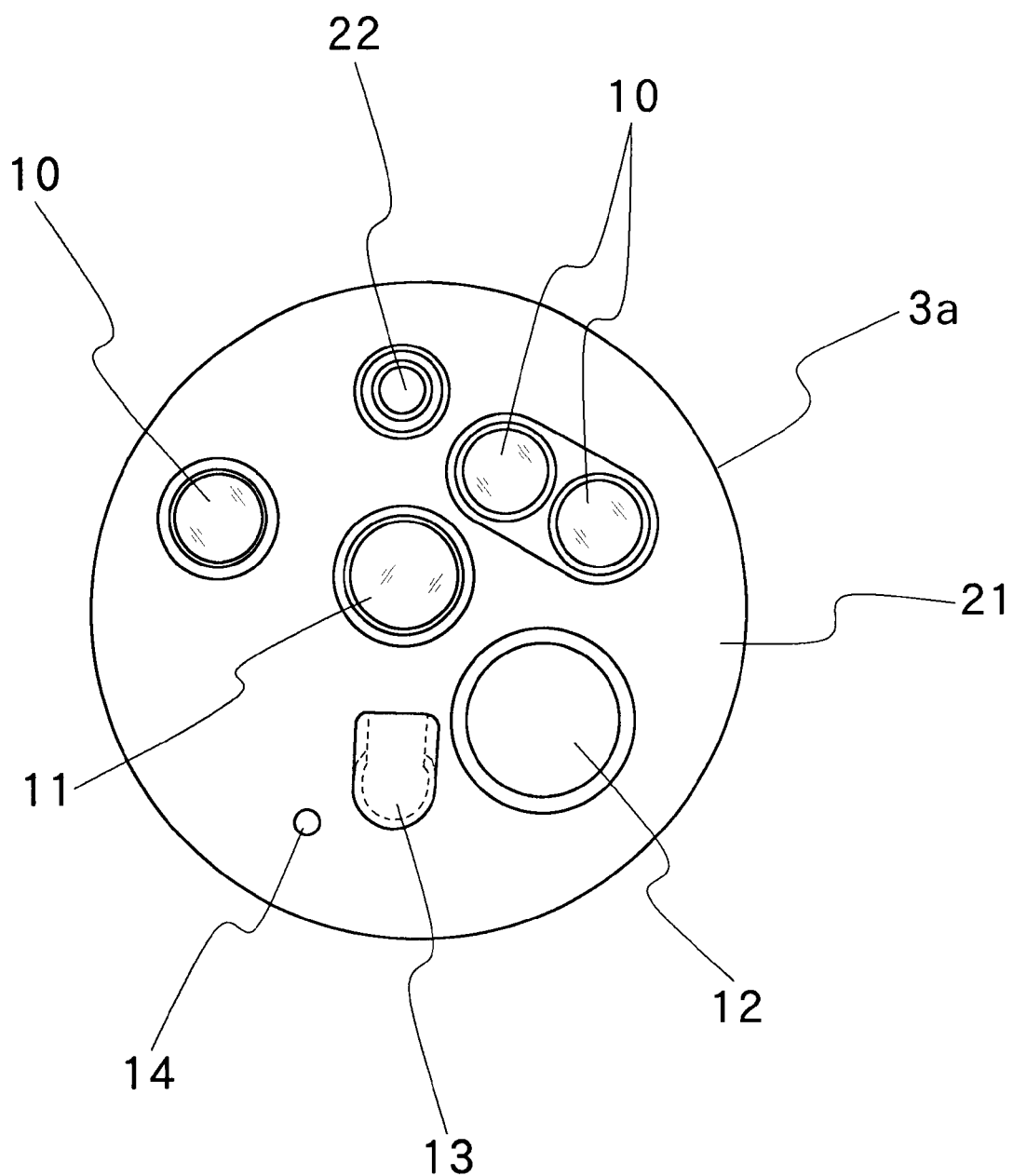
FIG. 2 is a schematic outer view of an end face of an insertion instrument of the endoscope.

As shown in FIG. 2, the rigid tip end section 3a has a housing of a rigid material, which is provided with illumination windows 10, an image pickup window 11, an outlet opening 12 of a biopsy channel, a wash fluid nozzle 13 and a jet water outlet 14 on its distal end face. In the particular embodiment shown, three illumination windows 10 are provided and located in three separate positions around the image pickup window 11. However, the number of the illumination windows 10 can be determined arbitrarily, and it is not a mandatory requisite to provide the jet water outlet 14. The angle section 3b functions to turn the rigid tip end section 3a upward, downward, leftward, rightward or in other arbitrary directions. The flexible rod portion 3c which occupies a major portion in the entire length of the insertion instrument 3 is flexible in bending directions but constructed to have sufficient strength against crushing forces. Namely, the flexible rod portion 3c is bendable in an arbitrary direction along a bend or bends which may exist in a path of insertion.

Figure 3:
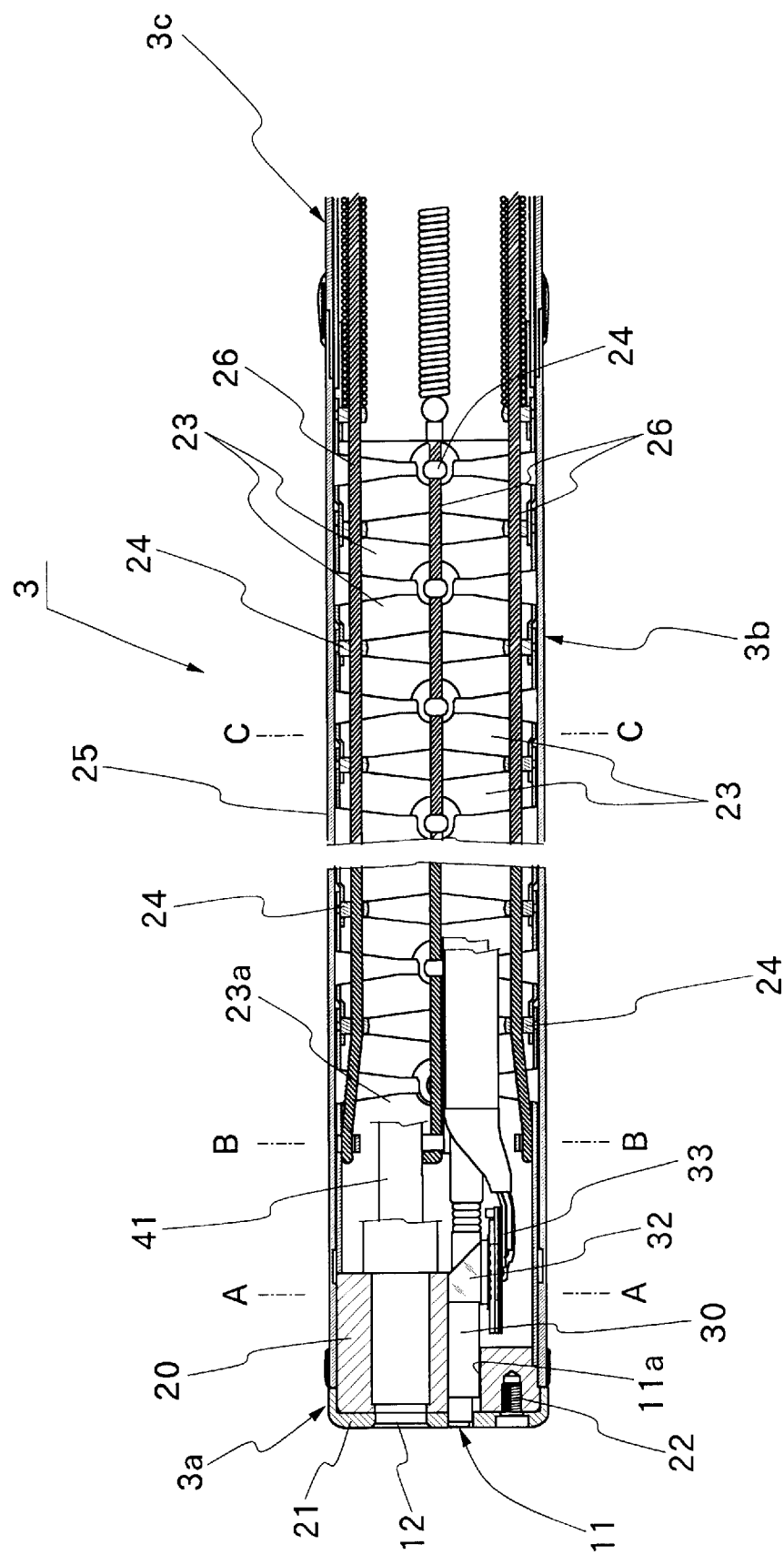
FIG. 3 is a fragmentary longitudinal sectional view of a fore end portion of the insertion instrument.

Shown in a longitudinal section in FIG. 3 is a fore end portion of the insertion instrument 3. As seen in that figure, the rigid tip end section 3a is provided with a mounter block 20 of a metallic material, for example. The mounter block 20 is bored with a plural number of axial through holes. Fitted on a distal fore end face of the mounter block 20 is an insulating cap 21, which is fixed to the mounter block 20 by screws 22. The angle section 3b is constituted by a large number of angle rings 23 which are successively connected into a jointed ring structure. The angle rings 23 of the jointed ring structure are enshrouded in a cover member 25 including a metal wire net or mesh layer and an outer skin layer which is formed of fluorine rubber, EPDM, urethane rubber or the like. Provided internally of the angle section 3b are four operating wires 26, which are operative in pairs, that is, operative in pairs in the vertical and lateral directions. Upon pulling in one of the operating wires which are paired in vertical direction while pushing out the other one, the angle section is bent in a vertical plane. On the other hand, upon pulling in one of the operating wires which are paired in a lateral direction while pushing out the other one, the angle section 3b is bent in a horizontal direction.

In this instance, of the large number of flexibly connected angle rings 23 of the angle section 3b, an end ring 23 in a foremost position is connected to the mounter block 20 of the rigid tip end section 3a. Accordingly, the insertion instrument 3 is rigid and unbendable from the distal end face of the insulating cap 21 to a pivoting joint portion of the foremost ring member 23a with a next ring member 23a of the angle section 3b.

As well known in the art, each illumination windows 10 illuminate a body cavity under examination with light rays which are transferred thereto through a light guide since body cavities are dark and can only be examined under a suitably illuminated state. An intracavitary site of interest is examined through the image pickup window 11 which is located substantially at the center of an end face of the rigid tip end section 3a of the insertion instrument 3. Consequently, the center of observation view field is located approximately on the center axis of the insertion instrument 3, and this is advantageous from the standpoint of inserting operations through a duct or canal. Besides, in case a hood is fitted on the rigid tip end section 3a, the obstruction of the observation view field by the hood can be suppressed to a minimum. Taking these into consideration, the image pickup window 11 at the distal end of the rigid tip end section 3a is arranged as explained below with reference to FIGS. 4 through 7.

Figure 4:
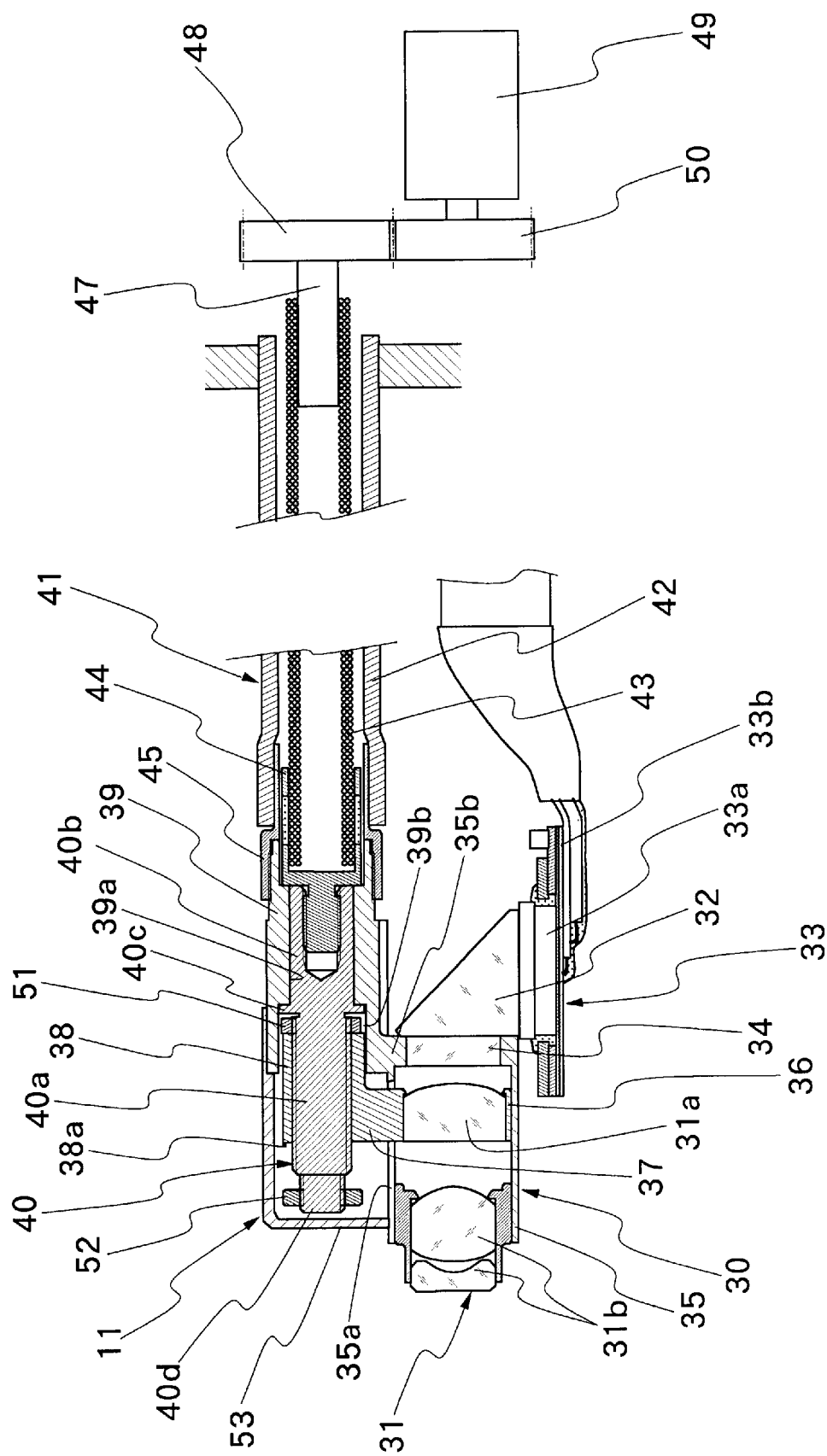
FIG. 4 is a schematic longitudinal sectional view of a drive mechanism for a movable lens of an objective lens system mounted on an image pickup assembly block at the fore distal end of the insertion instrument.

Firstly, indicated at 30 in FIG. 4 is an objective lens assembly which constitutes an objective lens system of the endoscope. The objective lens assembly 30 is mounted on an mounter block 11a (FIG. 3) which is provided on the mounter block 20. The objective lens system of the lens assembly 30 is constituted by an objective lens group 31 and a prism 32 which turns the light path from the objective lens group 31 downward through 90 degrees. Located at the focus of the objective lens group 31 is a solid-state image sensor assembly 33, including a solid-state image sensor device 33a which is cemented to the prism 32 and a substrate 33b of the solid-state image sensor device 33a. The use of the prism 32 which bends the light path at right angles as described above makes it possible to locate a light receiving surface of the solid-state image sensor device 33a and faces of the substrate 33b parallel with the axis of the insertion instrument 3. Further, interposed between the objective lens group 31 and the prism 32 is a filter 34 of suitable optical properties, along with a stop (not shown).

Figure 5:
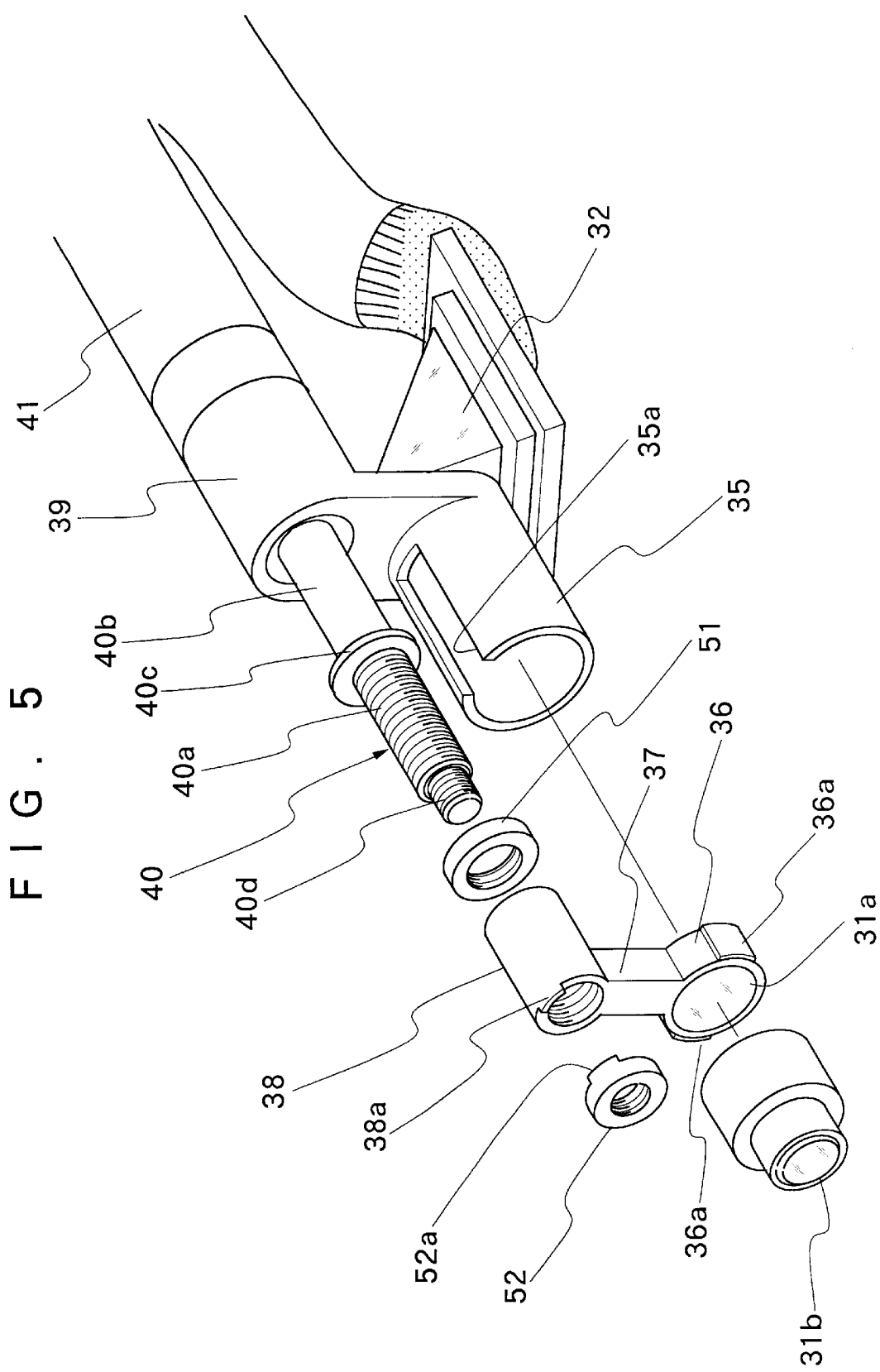
FIG. 5 is an exploded perspective view of a lens assembly block.
Figure 6:
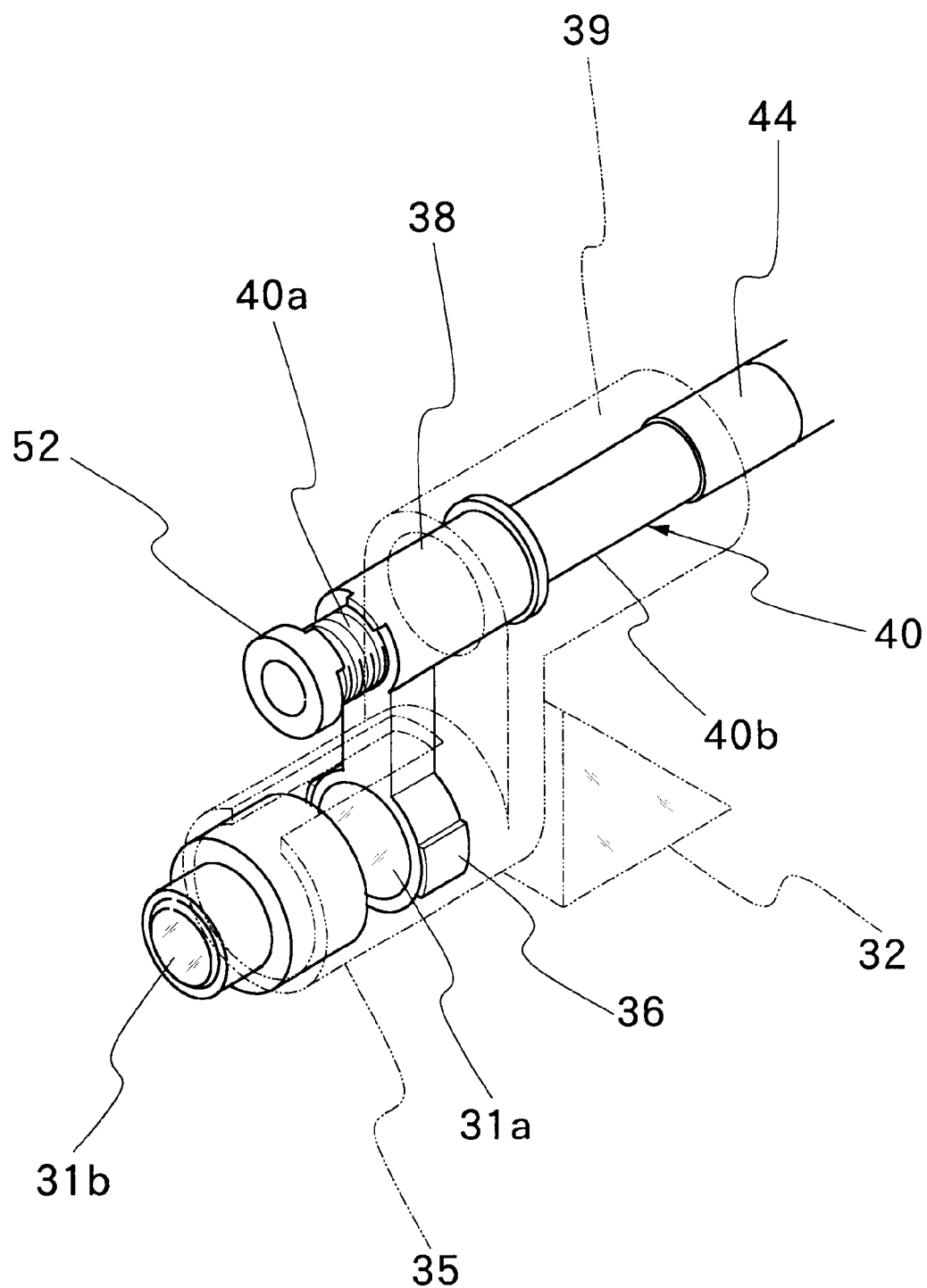
FIG. 6 is a perspective view of the lens assembly block in an assembled state.
Figure 7:
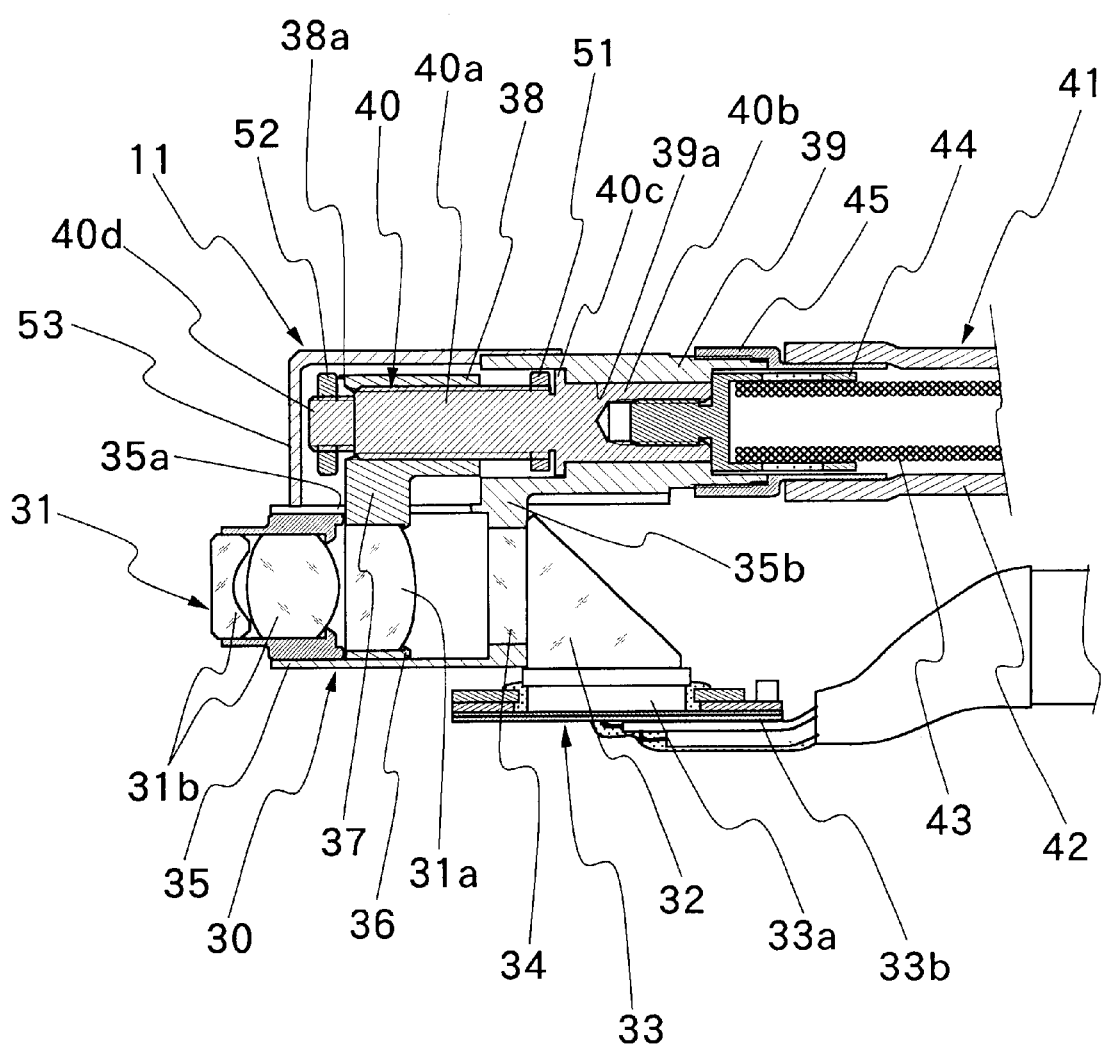
FIG. 7 is a sectional view similar to FIG. 4, showing the movable lens in an advanced position.

As clear from FIGS. 5 to 7, a lens 31a (a single lens element or more than one lens element) of the objective lens group 31 is movable in the direction of the optical axis, while the remainder lens elements 31b of the objective lens group 31 are fixed. The plural number of fixed lenses 31b are assembled into an independent lens tube and fixedly mounted on a lens support frame 35 which constitutes a fixed lens frame. The lens support frame 35 is bonded to front surface portions of the prism 32. The movable lens 31a is mounted on a movable lens frame 36 which is slidable along inner surfaces of the fixed lens support frame 35, for movement in the direction of optical axis. Thus, the lens assembly 30 includes the objective lens group 31, the lens support frame 35 which fixedly supports the fixed lenses 31b, and the movable lens frame 36 which supports the movable lens 31a.

In order to hold the movable lens 31a exactly in alignment with the optical axis of the fixed lenses 31b, the movable lens frame 36 for the movable lens 32a is fitted in the lens support frame 35 which permits the movable frame 36 to move only in the direction of the optical axis and prohibits movements in other directions, particularly movements in a direction perpendicular to the optical axis or movements in a falling direction In addition, the movable lens frame 36 is provided with sliding surface portions 36a at least at two positions on its outer peripheral surfaces. Namely, the movable lens frame 36 is held in sliding contact with inner surfaces of the lens support frame 35 only at the sliding surface portions 36a to minimize the contacting surface areas between the movable lens frame 36 and the lens support frame 35 and to guarantee smooth sliding movements. In the particular embodiment shown, the sliding surface portions 36a are arranged to have a predetermined width in the circumferential direction and located in two positions which are separated from each other in the circumferential direction by 180 degrees. The movable lens frame 26 is provided with an arm portion 37 which is extended out therefrom in a direction perpendicular to the optical axis. This arm portion 37 is projected to the outside through a slot 35a which is formed in the lens support frame 35 in the direction of the optical axis. A nut portion 38 is contiguously provided at the projected outer end of the arm 37. In this instance, the arm 37 has a thickness which substantially corresponds to the width of the slot 35a, so that it acts to restrict movements of the movable lens frame 36 in rotational direction.

With the arrangements as described above, the movable lens frame 35 is almost completely restrained from movements in rotational direction. The nut portion 38 is in threaded engagement with a screw rod 410, so that the movable lens frame 36 can be moved in the direction of the optical axis by moving the nut portion 38 along the screw rod 40 in a direction parallel with the optical axis. The reason why the movable lens frame 36 is made movable in the direction of the optical axis is to make it possible to vary at least one of focal depth, image magnification and view field angle of the objective lens system. In this connection, in order to let the movable lens frame 36 move smoothly in a stabilized state, the nut portion 38 is engaged with the screw rod 40 over as large a length as possible. The arm portion 37 is arranged to have a thickness which substantially corresponds to the length of the movable lens frame 36 in the direction of the optical axis, except the nut portion 38 which is elongated in a predetermined degree in the direction of the optical axis from its joint portion with the projected outer end of the arm portion 37.

The movable lens 31a is moved in the direction of the optical axis by remote control from the manipulating head assembly 2 of the endoscope. For this purpose, the lens support frame 35 is provided with a riser portion 36b, and a substantially cylindrical bearing member 39 is fixedly connected to the riser portion 36b. The bearing member 39 functions as a support for a drive means which moves the movable lens frame 36. The drive means includes a the nut portion 38 and the screw rod 40, which are provided contiguously on the projected outer end of the arm 37, and a control cable 41 which is arranged to rotate the screw rod 40. The screw rod 40 is divided into a screw rod portion 40a and a rotating shaft portion 40b. The rotating shaft portion 40b is rotatably received in an axial through hole 39a which is bored in the bearing member 39, immovably in the axial direction. The screw portion 40a projected forward over a predetermined length and from a predetermined distance from the bearing member 39, and held in threaded engagement with the nut portion 38. The nut portion 38 is provided with a rear extension which is projected largely on the rear side of the movable lens frame 36 toward the proximal end of the insertion instrument 3. The just-mentioned extension is received in a receptacle portion 39b which is bored into the bearing member 39 and in the form of an opening having an diameter lager than the outside diameter of the nut portion 38. This arrangement makes it possible to shorten the length of the drive means in the direction of the optical axis.

The above-mentioned control cable 41 includes a flexible sleeve 42, and a flexible rotation transmission shaft 43 which is fitted in the sleeve 42. The flexible transmission shaft 43 is constituted by tightly wound coils of II metal wires, more specifically, by inner and outer coils which are wound in opposite directions for turning the movable lens 31a in forward and reverse directions, respectively. Consequently, the flexible transmission shaft 43 is flexible in bending directions and capable of transmitting rotation to its fore distal end securely through the tightly wound coils. Therefore, in terms of transmission of rotation, the flexible shaft 43 is substantially in a rigid form and remains in that form even if it is flexed into a bent shape. The fore distal end of the flexible transmission shaft 43 is connected to the screw rod 40 by a connecting member 44, while the fore distal end of the sleeve 42 is fixedly connected to the bearing member 39. Accordingly, when the proximal end of the flexible transmission shaft 43 is caused to turn about its axis within the sleeve, this rotation is transmitted to the screw rod 40 to rotate the nut portion 38 along with the movable lens frame 36 which is connected to the nut portion 38.

When in rotation, the flexible transmission shaft 43 is held in sliding contact with inner surfaces of the sleeve 42. In order to ensure smooth rotation of the flexible shaft 43, preferably the sleeve 42 is lubricated by the use of a lubricant or by a lubricative treatment at least on its inner surfaces to reduce the friction of sliding surfaces. As for a lubricative treatment, in case the sleeve 42 is of silicon rubber, more particularly, of galvanizing type silicon rubber, for instance, methyl phenyl silicon oil may be impregnated thereinto. Of course, it is possible to use other material for the sleeve and for the lubricative treatment. In addition to or instead of inner surfaces of the sleeve 42, the lubricative treatment can be made to sliding surfaces of the flexible shaft 43. However, in view of the difficulty of sealing the inside of the sleeve 42 into a fluid-tight state, it is not desirable to use molybdenum disulfide powder or lubricant oil or other liquid lubricative agents.

The screw rod 40 is rotatable but should be retained in a blocked state against movements in the axial direction. For this purpose, a flange portion 40c is provided between the screw portion 40a and journal portion of the screw rod 40. This flange portion 40c has an outside diameter larger than the axial through hole 39a of the bearing member 39. On the other hand, connected in threaded engagement with a proximal end portion of the screw rod 40 is a connecting member 44 which has an outside diameter larger than the axial hole 39a. As a consequence, the flange portion 40c and the connecting member 44 are abutted against the bearing member 39 at the fore and rear ends of the axial through hole 39a, respectively, to block movements of the screw rod 40 in the axial direction. However, if the connecting member 44 is pressed against the bearing to an excessively degree, it could increase the resistance against rotation of the screw rod 40. Accordingly, it is desirable to set the screw rod 40 in position in such a way as to permit substantially no play in the axial direction, without applying thereto pressing forces from the flange portion 40c and the connecting member 44 which are in abutting engagement with the opposite end faces of the bearing member 39.

The proximal end of the control cable 41 is passed through the insertion instrument 3 and extended into the manipulating head assembly 2. Within the manipulating head assembly 2, the proximal end of the flexible transmission shaft 43 is connected to a rotational drive shaft 47, while the proximal end of the sleeve 42 is securely fixed to a casing or other fixed structure of the manipulating head assembly 2. Mounted on the rotational shaft 47 is a follower gear 48 which is meshed with a drive gear 50 which is in turn mounted on an output shaft of a motor 49. As the motor 49 is actuated and the drive gear 50 is put in rotation, the follower gear 48 is caused to follow the rotation of the drive gear 50. As a result, the rotational shaft 47 and the flexible transmission shaft 43, which is coupled with the rotational shaft 47, are rotated about the respective axes, rotationally driving the screw rod 40 which is connected to the flexible transmission shaft 47 and thus driving the movable lens 31a in the direction of optical axis. In order to control the operation of the motor 49, a lens control means 5 is provided on the manipulating head assembly 2. For example, this lens control means 5 is constituted by an operating button or by a toggle switch or the like. The lens control means 5 is pushed for on-off control of the motor 49. Particularly in the case of a toggle switch, the movable lens 31a can be located in a halfway position within its stroke range. If desired, arrangements may be made to manually rotate the flexible transmission shaft 43.

Thus, the movable lens 31a is movable between a rear position on the side of an imaging plane, as shown in FIG. 4, and a fore position on the side of a subject, as shown in FIG. 7. When the movable lens 31a is located in the rear position, the objective lens system has a smaller image multiplication rate and a wider view field angle. In contrast, the image multiplication rate becomes larger and the view field angle becomes smaller when the movable lens 31a is located in the fore position on the side of a subject. Besides, the focal depth changes depending upon the position of the movable lens 31a, namely, becomes shallower toward the fore position on the side of a subject. Therefore, after introducing the endoscopic insertion instrument 3 into a body cavity, the position of the movable lens 31a is located either in the fore position or rear position according to the nature of a diagnostic or therapeutic treatment. When shifting the position of the movable lens 31a by way of the control cable 41, it has to be located exactly either in the rear position on the imaging side or in the front position on the subject side.

For this purpose, the movable lens 31a has to be moved constantly along the optical axis of the objective lens group 31 as a whole, namely, axially in alignment with the fixed lens 31b. This is why the sliding surface portions 36a of the movable lens frame 36 are moved in sliding contact with inner surfaces of the lens support frame 35 of the fixed lens 31b. The both of the sliding surface portions 36a which are provided in two different positions on the movable lens frame 36 are substantially held in surface contact with the lens support frame 35. Nextly, it is necessary to hold the movable lens 31a against spontaneous movements in the rotational direction during a shift to the front or rear position. For this purpose, the arm portion 37 is formed in a thickness which just fits in the slot 35a of the lens support frame 35 without a play for blocking rotational movements of the movable lens frame 36 relative to the lens support frame 35. Consequently, the movable lens 31a can be located in the front or rear position in an extremely accurate manner, and substantially blocked against movements other than movements in the direction of optical axis.

As described above, by applying a driving force to the nut portion 38 which is contiguously provided on the arm portion 37 of the movable lens frame 36, the movable lens 31a is shifted either to the rear position on the imaging side or to the front position on the subject side with extremely high accuracy. This positioning of the movable lens 31a is effected by means of the screw rod 40 and the nut portion 38. The movable lens 31a can also be stopped in predetermined positions by providing stoppers on the lens support frame 35. However, it is more desirable to provide positioning means on the part of the screw rod 40 because the driving force for the movable lens 31a is applied through the screw rod 40.

In this instance, the screw rod 40 is engaged with the nut portion 38 to translate a rotational movement into a linear movement. In the particular embodiment shown, a pair of stopper rings 51 and 52 are provided on fore and rear portions of the screw rod 40. One stopper ring 51 functions as a positioning means which locates the movable lens 31a in the rear position on the imaging side, and the other stopper ring 51 as another positioning means which locates the movable lens 31a in the front position on the subject side. Namely, the two stopper rings 51 and 52 delimit the stroke range of the nut portion 38. Therefore, these stopper rings 51 and 52 actually function to position the nut portion, and do not function to position the movable lens 31a directly. Therefore, it is important to preclude the influences of errors which might occur in an assembling stage. Therefore, the image pickup assembly 11 is arranged such that, after assembling its respective parts together, positions of the two stopper rings 51 and 52 can be adjusted before connecting it to the rigid tip end section 3a of the insertion instrument 3.

The stopper rings 51 and 52 can be applied in various forms. In the case of the particular example shown, the stopper rings 51 and 52 are arranged in different forms. Namely, the stopper ring 52 which determines the position of the movable lens 31a on the imaging side is threaded on the screw portion 40a of the screw rod 40. Accordingly, the movable lens 31a is stopped precisely in the rear position on the imaging side by abutment of the nut portion 38 against the stopper ring 51. The stop position on the imaging side can be adjusted by turning and adjusting the position of the stopper ring 51 on the screw portion 40a in the forward or rearward direction. However, if the stopper ring 51 is in a free state in the rotational direction, it can be turned with rotation of the nut portion 38. Therefore, it is desirable to set a stopper screw in the annular body of the stopper ring 51 or to fix the stopper ring 51 in position by the use of an adhesive or by spot welding after adjusting its position on the screw portion 40a.

On the other hand, the stopper ring 52 which determines the position of the movable lens 31a on the side of the subject is axially adjustably threaded on a second screw portion 40d which is axially projected from the fore end of the screw portion 40a. As compared with the screw portion 40a, the screw thread of the second screw portion 40d is formed in the opposite direction or in a different feed pitch. Consequently, as the nut portion 38 is brought into abutting engagement with the stopper ring 52, there is no possibility of the stopper ring 52 being turned together with the nut portion 38. Especially when the movable lens 31 a in the front position on the side of the subject, the focal depth of the objective lens group 31 becomes shallower. This means that the movable lens 31a should be located more accurately in the front position than in the rear position on the imaging side. Besides, its positional adjustments should be permitted after assembling the image pickup 11. Since the nut portion 38 is threaded on the screw portion 40a, it is desirable to employ the arrangements as shown in FIGS. 8 and 9 in order to stop the nut portion 38 more accurately in a predetermined stop position.

Figure 8:
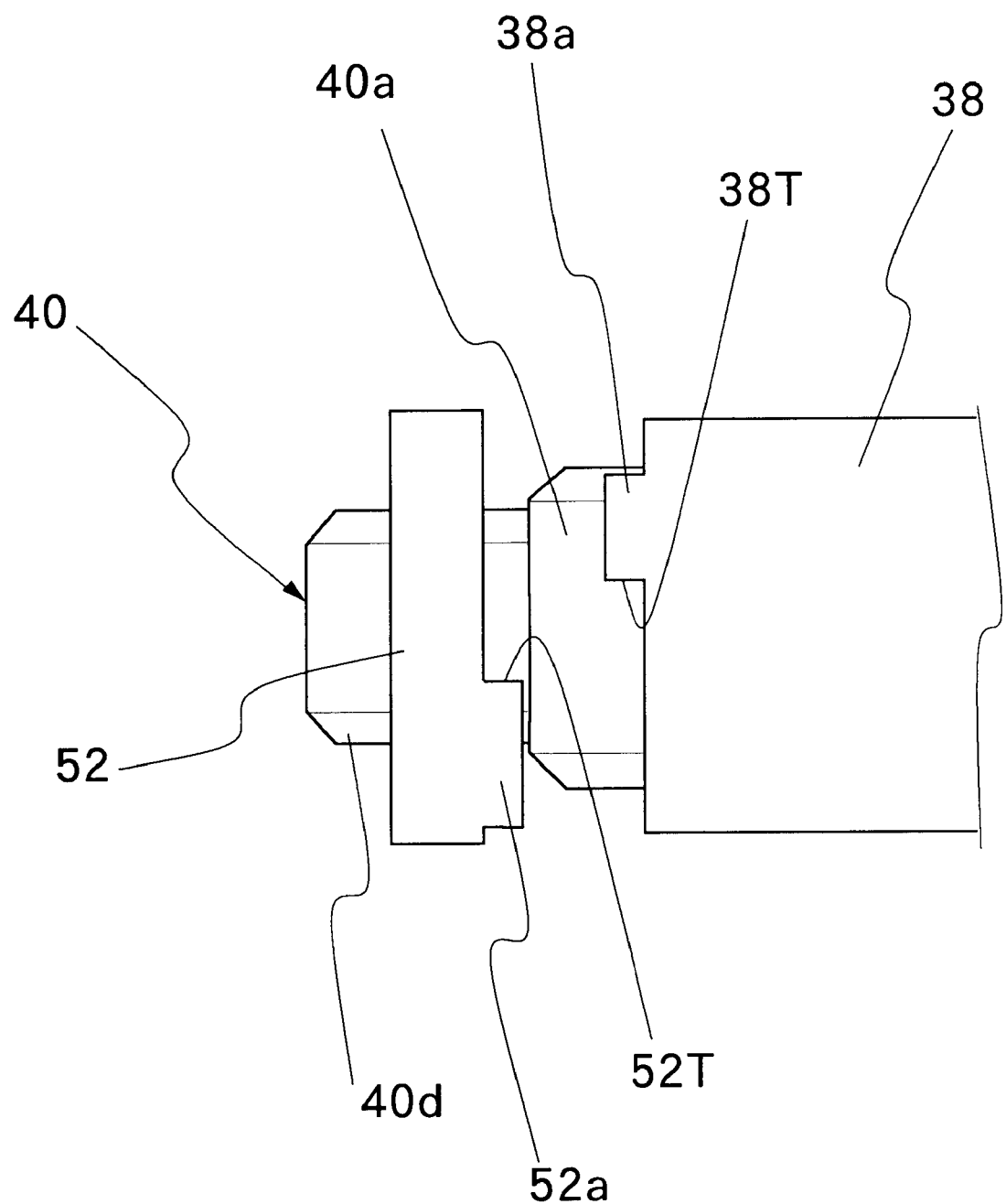
FIG. 8 is a schematic illustration explanatory of conditions of a nut portion and a stopper ring to be brought into fitting engagement with each other.

As seen in FIGS. 8 and 9, the stopper ring 52 is provided with an axially projecting land portion 52a in a sectoral part of its inner end face, while the nut portion 38 is provided with an axially projecting land portion 38a in one sectoral part of its outer end face on the side of the stopper ring 52. These land portions 52a and 38a are provided with radial meeting surfaces 52T and 38T to be engaged with each other. These radial surfaces 52T and 38T function as positioning walls which stop the nut portion 38 in a predetermined position. Fine adjustments of the position of the nut portion 38 can be made by applying a pressing force to the nut portion 38 in a rotational direction as indicated by an arrow in FIG. 9.

Since the movable lens frame 36 is driven by way of the screw rod 40 and the nut portion 38 which are in threaded engagement with each other, it is important to maintain the engagement of these members in as good conditions as possible. For example, deposition of foreign matter or of a contaminant may occur to the engaging surfaces of the screw rod 40 and/or nut portion 38 as the control wire 26 is pulled in and out to flex the angle section 3b of the insertion instrument 3, deteriorating the conditions of the threaded engagement to such a degree as to hinder smooth movements of the nut portion 38. In order to avoid a problem of this sort, the screw rod 40 and the nut portion 38 are hermetically housed in a protective cover 53 which is arranged to rise upward from a fore end portion of the lens support frame 35 and extend toward and into fitting engagement with a fore end portion of the bearing member 39.

The entire assembly of the optical objective lens system as described above is fitted into a fore end portion of the endoscopic insertion instrument 3. More specifically, the fixed lens 31b is once removed to fit the movable lens support frame 36 into the lens support frame 35 along with the movable lens 30a. Prior to insertion into the lens support frame 35, the stopper ring 51 is threaded onto the screw rod 40, and the nut portion 38, which is formed integrally with the movable lens frame 36, is threaded onto the screw portion 40a of the screw rod 40. Further, the stopper ring 51 is threaded onto the second screw portion 40d. In this state, the movable lens frame 36 is inserted into the lens support frame 35, and the arm portion 37 of the movable lens frame 36 is projected to the outside through the slot 35a.

Upon inserting the movable lens frame 36 into the lens support frame 35, the rotating shaft portion 40b of the screw rod 40 is fitted into the bore 39a of the bearing member 39, which is provided integrally with the lens support frame 35. As soon as the flange portion 40c of the screw rod 40 comes into abutting engagement with an end face of the bearing member 39, the rotating shaft portion 40b is passed through the bore 39a of the bearing member 39. In this state, the connecting member 44 at the fore end of the flexible transmission shaft 43 is threaded into the rotating shaft portion 40b of the screw rod 40. Then, the connector ring 45 which is connected to the sleeve 42 is fixed to the bearing member 39 which is gripped between the connecting member 44 and the flange portion 40c. Further, an assembly of the objective lens group 31, including the fixed lens 31b and a lens tube, is assembled into a predetermined position within the lens support frame 35. Consequently, the respective components of the image pickup section 11, including the optical objective lens system and the solid-state image sensor assembly 33, are assembled together.

In this state, for the purpose of adjusting the positions of the stopper rings 51 and 52, the movable lens 31a is actually moved in the axial direction by rotating the flexible transmission shaft 43. In so doing, the nut portion 38 is moved to the rear position on the imaging side and into abutting engagement with the stopper ring 51, and at the same time the stopper ring 51 is adjust to a position where the sharpest images are available. The same adjustments are made also with regard to the front position on the side of the subject, bringing the nut portion 38 into abutting engagement with the stopper ring 52 and setting the stopper ring 52 in a position where the sharpest images are available. These adjustments can be made after assembling the optical objective lens system into the image pickup 11. After assembling the image pickup 11 in the manner as described above, it is assembled with and fixedly attached to the image pickup mounter 11a by the use of a set screws or the like.

After introducing the insertion instrument 3 of an endoscope 1 into a body cavity of a patient, for example, the image pickup 11 is located in such a position as to hold an entire intracavitary site of interest in its view field or located in a closer position to view part of the intracavitary site on an enlarged scale. In case part of an intracavitary site is examined closely, the magnification rate or view field angle is changed by manipulating the lens control means 5 which is provided on the manipulating head assembly 2. Namely, upon manipulating the lens control means 5, the motor 49 is actuated to rotate the flexible transmission shaft 43 of the control cable 41 within the sleeve 42. This rotation is transmitted to the screw rod 40. At this time, if the control cable 41 happens to be in a bent form, it is likely for the flexible shaft 43 to be held in sliding contact with inner surfaces of the sleeve 42. However, by a lubricating treatment of the inner surfaces of the sleeve 42, e.g., impregnation of methyl phenyl silicon oil, the flexible transmission shaft 43 can be rotated smoothly with less resistance to its rotation and under a light load despite the sliding contact with the sleeve 42.

As soon as the screw rod 40 is rotated, the nut portion 38 which is in threaded engagement with the screw portion 40a is put in movement. At this time, the nut portion 38 is not rotated because the arm portion 37 which is connected with the nut portion 38 is blocked against rotation by abutting engagement with inner surfaces of the slot 35a. Accordingly, the rotation of the screw rod 40 is translated into an axial movement of the nut portion 38, moving the movable lens frame 36 axially along inner surfaces of the lens support frame 35 toward or away from the fixed lens 31b to locate the movable lens either in the rear position on the imaging side or in the front position on the subject side.

The screw rod 40 is supported by the bearing member 39 which is provided integrally with the lens support frame 35.

In addition, the movable lens frame 36 is restricted of movements in both falling and rotational directions. Accordingly, the line of axis of the bore 39a of the bearing member 39 is located exactly in parallel relation with optical axis of the objective lens group 31, ensuring rectilinear drive by the screw rod 40. As a consequence, the movable lens frame 36 is invariably moved in the direction of optical axis without possibilities of disturbing axial alignment between the movable lens 31a of the objective lens group 31 and the fixed lens 31b.

In order to move the movable lens 31a accurately in the direction of optical axis, the sliding surface portions 36a of the movable lens frame 36 should be tightly engaged with inner surfaces of the lens support frame 25.

Therefore, sliding movements of the movable lens frame 36 are met by a relatively large resistance. By the threaded engagement of the nut portion 38 with the screw rod 40, the rotation of the flexible shaft 43 which constitutes part of the control cable 41 is translated into linear movement of the movable lens 31a. Accordingly, not only at the time of shifting the movable lens 31a to the rear position on the imaging side but also at the time of shifting the movable lens to the front position on the subject side, it can be driven by application of substantially same driving force which way overcomes the resistance to sliding movement of the movable lens frame 36. Besides, it is possible to preset a necessary backlash in the threaded engaging portions of the screw rod 40 and the nut portion 38. Therefore, the threaded portions can absorb errors which might have occurred in machining and assembling stages, permitting the movable lens 31a to move accurately to the front or rear position without troubles despite existence of such errors.

The angle section 3b which is connected to the rigid tip end section 3a of the insertion instrument 3 can be manipulated. into a bent or flexed form. More specifically, the angle section 3b is flexed to a desired direction by pulling or pushing four operating wires 26 which are arranged at angular intervals of 90 degrees. The angle section 3b can be flexed in an upward or downward direction by pulling back one of vertically paired operating wires 26 while pushing forward the other one of the paired operating wires 26. On the other hand, the angle section 3b can be flexed in a lateral direction, by pulling back one of laterally paired operating wires 26 while pushing forward the other one of the operating wires 26. In this flexing operation, the angle section 3b has to be turned accurately into a desired direction.

Figure 10:
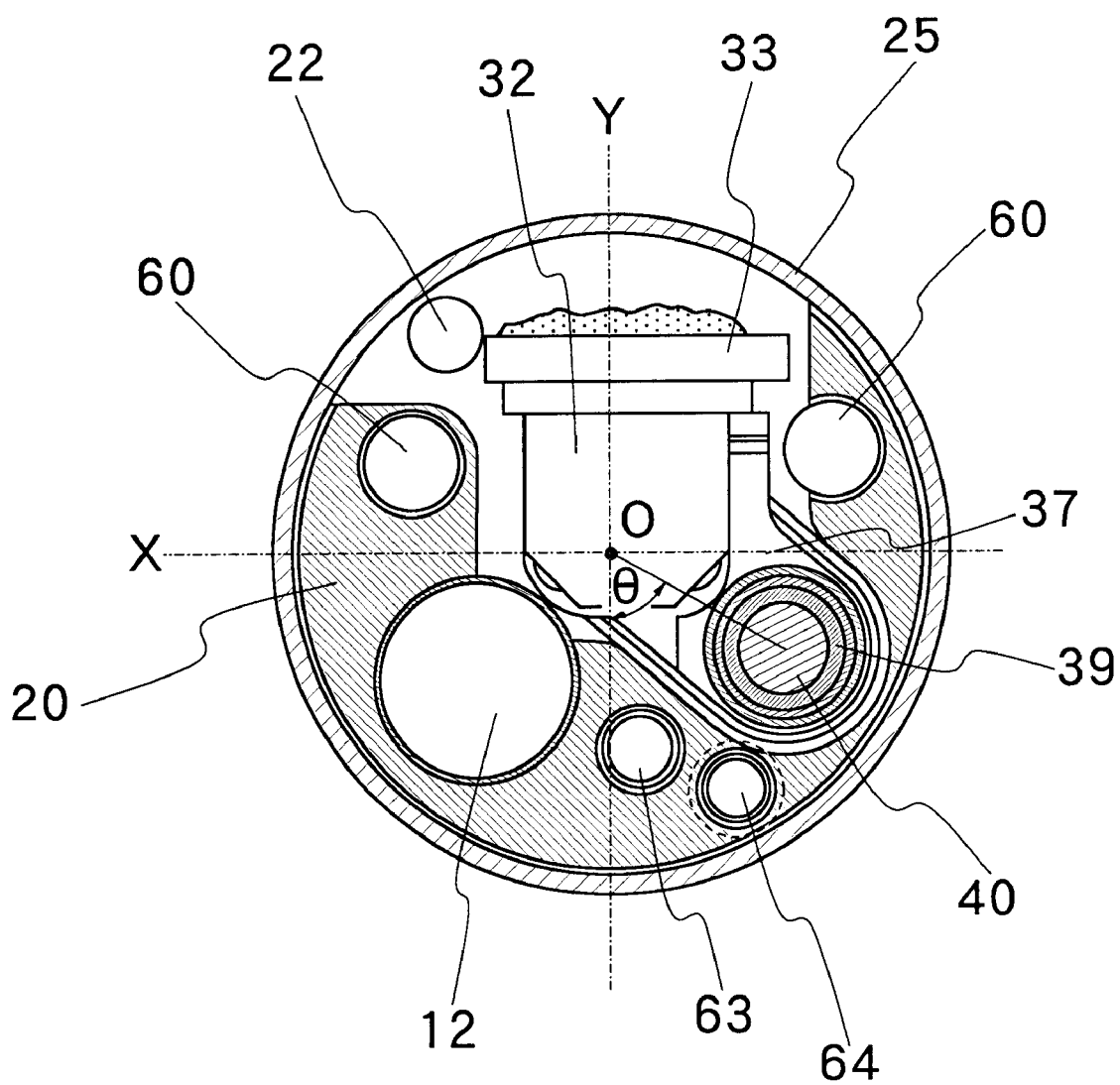
FIG. 10 is a schematic sectional view taken on line A—A of FIG. 3.
Figure 11:
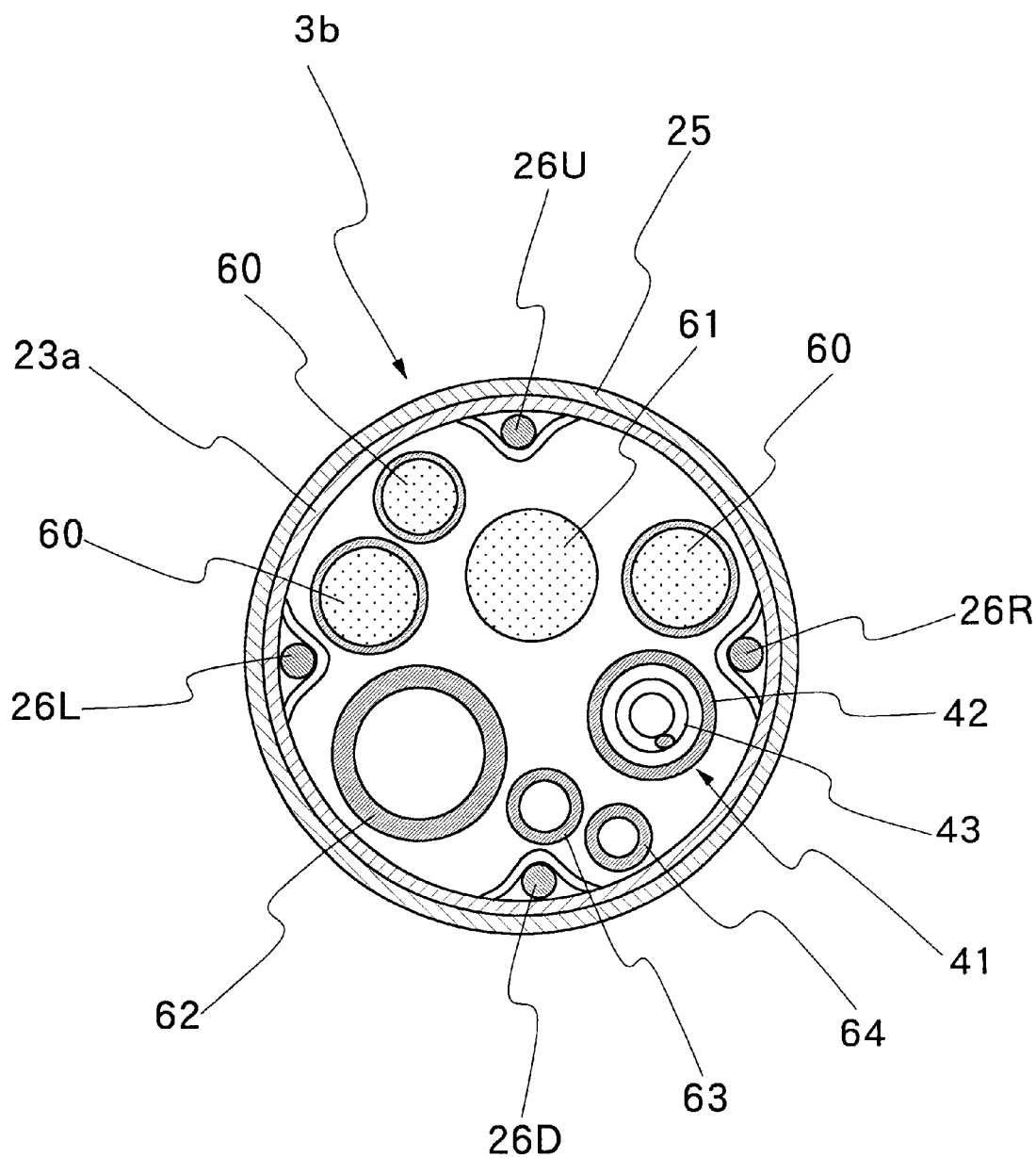
FIG. 11 is a schematic sectional view taken on line B—B of FIG. 3.
Figure 12:
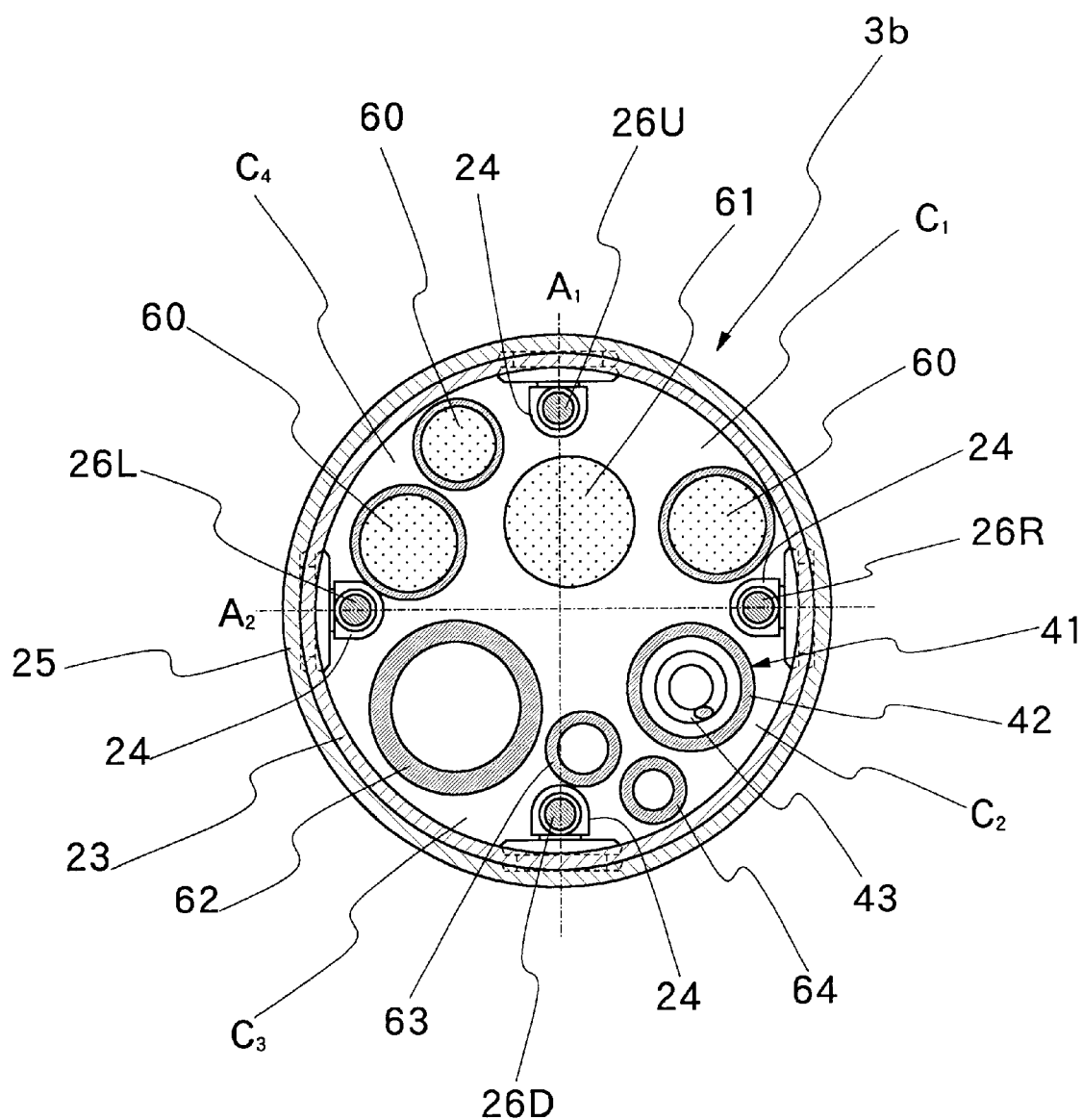
FIG. 12 is a schematic sectional view taken on line C—C of FIG. 3.
Figure 13:
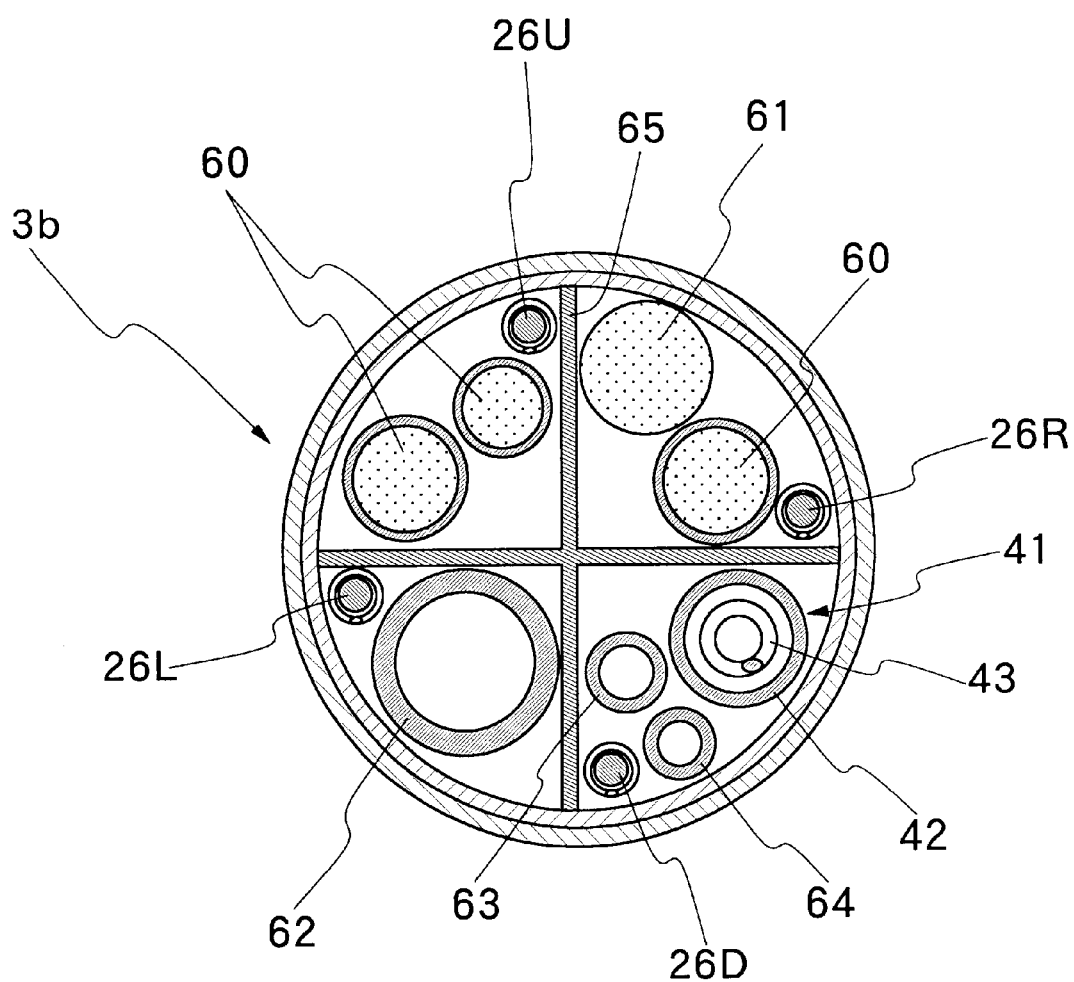
FIG. 13 is a view similar to FIG. 12 except that a spacer is fitted in an angle section to divide the latter into subdivisions for locating respective internally threaded component parts separately in predetermined positions.

As shown in FIGS. 10 to 12, various parts are threaded in the insertion instrument 3 of the endoscope. The internally threaded component parts include a light guide 60 which is connected to the illumination window 10, a signal cable 61 which is connected to a wiring substrate board 33b of a solid-state image sensor element 33a, a biopsy instrument channel 62 which is connected to an instrument outlet opening at the distal end of the insertion instrument 3, an air/water feed tube 63 which is connected to the washing nozzle 13; a jet feed tube 64 which is connected the jet feed nozzle 14, and a control cable 41. These internally threaded component parts are different from each other in flexibility in bending directions, and, among them, the hardest one is the biopsy instrument channel or biopsy channel 62 and the next hardest one is the control cable 41. Therefore, if these hard or stiff parts are concentrated in one particular region in a sectional area of the angle section 3b, it is very likely that, because of high resistance to bending motions in that particular region, the angle section 3b is flexed in a twisted state and becomes very difficult to control is flexing or bending direction. For this reason, the respective internally threaded component parts are located in a balanced state in terms of the resistance to bending motions and in such a way as to guarantee accurate flexing or bending operations of the angle section 3b without necessitating to increase the diameter of the insertion instrument 3 to any conspicuous degree.

With regard to positional relations of the internally threaded component parts, as seen in FIG. 10, the positions of the light guide 60, signal cable 61, biopsy instrument channel 62, air/water feed tube 63 and jet feed tube 64 depend on positions of corresponding parts in or on the rigid tip end section 3. Since the internally threaded component parts are flexible, it is possible to change their positions within the angle section 3b to a certain degree but drastic changes of their position are extremely difficult or infeasible. In this regard, the control cable 41, which moves the movable lens frame 35 of the lens assembly 30 of the optical objective lens system which is located substantially centrally of the rigid tip end section 3a, is adapted to drive the nut portion 38 on the arm portion 37 which is extended out from the movable lens frame 35. It follows that the arm portion 37 can be extended in a desired direction.

Considering the locations of various internally threaded component parts in connection with two perpendicularly intersecting vertical and horizontal axes X and Y which pass through a center O of a sectional area of the endoscopic insertion instrument 3, taken perpendicularly to its longitudinal axis, the vertical axis Y corresponds to the direction of vertical flexing movement of the angle section 3b and the horizontal axis X corresponds to the direction of lateral flexing movement. The arm portion 37 is tilted to the right from the vertical axis by an angle θ. The control cable 41 is located in an off-set position in the rotational direction from the vertical axis Y, namely, from a center line of vertical flexing movement. The exact position of the control cable 41 is determined depending upon positional relationship with the biopsy instrument channel 62 which is the hardest member in terms of stiffness in bending directions. For instance, in the case of the arrangements shown in FIG. 12, the biopsy instrument channel 62 is located in a position obliquely on the left side of the vertical axis Y.

As shown in FIGS. 11 and 12, four operating wires 26 are provided within the angle section 3b, including upper operating wire 26U, lower operating wire 26D, and right and left operating wires 26R and 26L. As seen particularly in FIG. 12, the interior space of the angle section 3b can be divided into four subdivisions $C_1$ to $C_4$, by two straight lines A1 and A2 which are drawn between the operating wires 26U and 26D and between the operating wires 26R and 26L, respectively, in a plane perpendicular to the center axis of the angle section 3b, and the respective internally threaded component parts of the insertion instrument are distributed to the four subdivisions $C_1$ to $C_4$ of the angle section 3b in a balanced state.

More specifically, of the above-mentioned internally threaded component parts, the biopsy instrument channel 62 which is largest in diameter and less flexible is substantially solely located in the subdivision $C_3$. Located in the subdivision $C_2$ is the control cable 41 which is secondly largest in diameter, depending upon the projecting direction of the arm portion 37, and which has relatively high resistance to bending movements. Further located in the subdivision $C_2$ are the air/water feed tube 63 and the jet feed tube 64. Consequently, the internally threaded component parts are distributed in a balanced state on the opposite sides of the straight line A1 in terms of resistance to bending movements. In this instance, the control cable 41 and jet feed tube 63 are located completely within the subjection $C_2$, but the air/water feed tube 63 is located partly in the subdivision $C_2$ and partly in the subdivision $C_3$. This arrangement reflects the difference between the control cable 41 and the air/water feed tube 63 in the degree of hardness or stiffness in bending directions. If the difference is greater, the air/water feed tube 63 is completely located in the subdivision $C_2$. If smaller, the position of the air/water feed tube 63 is shifted toward the subdivision $C_3$. Namely, the air/water feed tube 63 can function as a balancing element the position of which can be shifted for the purpose of balancing the bending resistance.

Located in the remainder subdivisions $C_1$ and $C_4$ are three light guides 60 and one signal cable 61, which are relatively flexible in bending directions and therefore can be located somewhat in a dispersed fashion. However, in consideration of fragility, these internally threaded component parts should preferably be located on the opposite side of the line A2 away from relatively hard threaded members such as the biopsy instrument channel 62, control cable 41, air/water feed tube 63 and jet feed tube 64. In the particular example shown, two light guides 60 are located in the subdivision $C_4$, while the third light guide 60 is located in the subdivision $C_1$, and the signal cable 41 is located in a position between the subdivisions $C_1$ and $C_4$ and slightly closer to the subdivision $C_1$, for balancing purposes.

With the arrangements as described above, internally threaded component parts in the form of a relatively stiff tube are located in the lower subdivisions $C_2$ and $C_3$, while internally threaded component parts which are fragile or which can be easily broken under pressure like a bundle of fine fiber optics are located in the upper subdivisions $C_1$ and $C_4$. Therefore, as compared with a case where the internally threaded component parts are located in a random fashion, it becomes possible to prevent compressive damages to fragile internally threaded component parts without providing an ample space for them. Consequently, the above-described arrangements permits to utilize the inner space of the angle section effectively and to prevent breakage of fine fiber optics or bucking of tubes or the like which are threaded at a relatively high packing rate.

As described above, the internally threaded component parts are distributed to the subdivisions $C_1$ to $C_4$ within the angle section 3b. In order to retain these threaded members stably in the respective positions, a connector ring 26 with a cross-shaped spacer member 65 is interposed between the angle section 3b and the flexible rod portion 3c. In this case, by the spacer member 65, the internally threaded component parts are restricted to the respective predetermined positions. Accordingly, the internally threaded component parts which are fixed to the rigid tip end section 3a at the respective fore ends are retained in position in a restricted state by the spacer member 65 in the respective proximal end portions. Therefore, even if the angle section 3b is repeatedly flexed into a largely bent form, there is no possibility of the internally threaded component parts being pressed against each other or getting entangled with each other. In this regard, although the spacer member 65 can be formed of a synthetic resin material, but the spacer member 65 is preferred to be of hard rubber or similar material which undergoes elastic deformation to a certain degree but normally has suitable rigidity. Within the angle section 3b, the signal cable 61 is increased in outside diameter and located partly in the subdivision $C_1$ and partly in the subdivision $C_4$. On the part of the flexible rod portion 3c which is bent in a less degree, the signal cable 61 is wrapped more strongly and pulled toward the subdivision C1.

The angle section 3b of the insertion instrument can be flexed in upward and downward directions as well as in rightward and leftward directions in case the respective internally threaded component parts are positioned in a balanced state within the angle section 3b as described above. In this case, the angle section 3b is arranged to have small resistance to upward bending movements but to have greater resistance to downward bending movements, and balanced in resistance to rightward and leftward bending movements. Accordingly, in overall the angle section 3b has resistance to flexure mainly in the direction of the line $A_1$ or $A_2$ and therefore has no possibilities of getting twisted during flexing or bending operations. It follows that, when the angle section 3b can be flexed or bent precisely as the angle knob 5 is manipulated for a flexing or bending operation. This improves the controllability of the angle section 3b when it is flexed or bent at the time of introduction into a body cavity in order to turn the rigid tip end section 3b into a desired direction along a path of insertion or in order to change the direction of the observation view field.

Almost all of relatively hard threaded members are located on the lower side of the line A2 which divides the internal space of the angle section 3b into upper and lower portions. As a consequence, the angle section 3b can be bent in an upward direction more easily than in other directions because internally threaded component parts with higher flexibility are located on the side of the angle section which is bent more acutely than the other side where relatively resistive parts are located. At the time of changing the direction of the view field of the endoscopic image pickup within an internal organ, for instance, it is often the case that the angle section 3b is required to be bent more frequently and to a greater degree in an upward direction than in other directions. Accordingly, in order to improve the controllability of the endoscopic insertion instrument as a whole, it is extremely rational to locate relatively flexible internally threaded component parts in upper portions and relatively stiff or resistive internally threaded component parts in lower portions of the insertion instrument.

Figure 14:
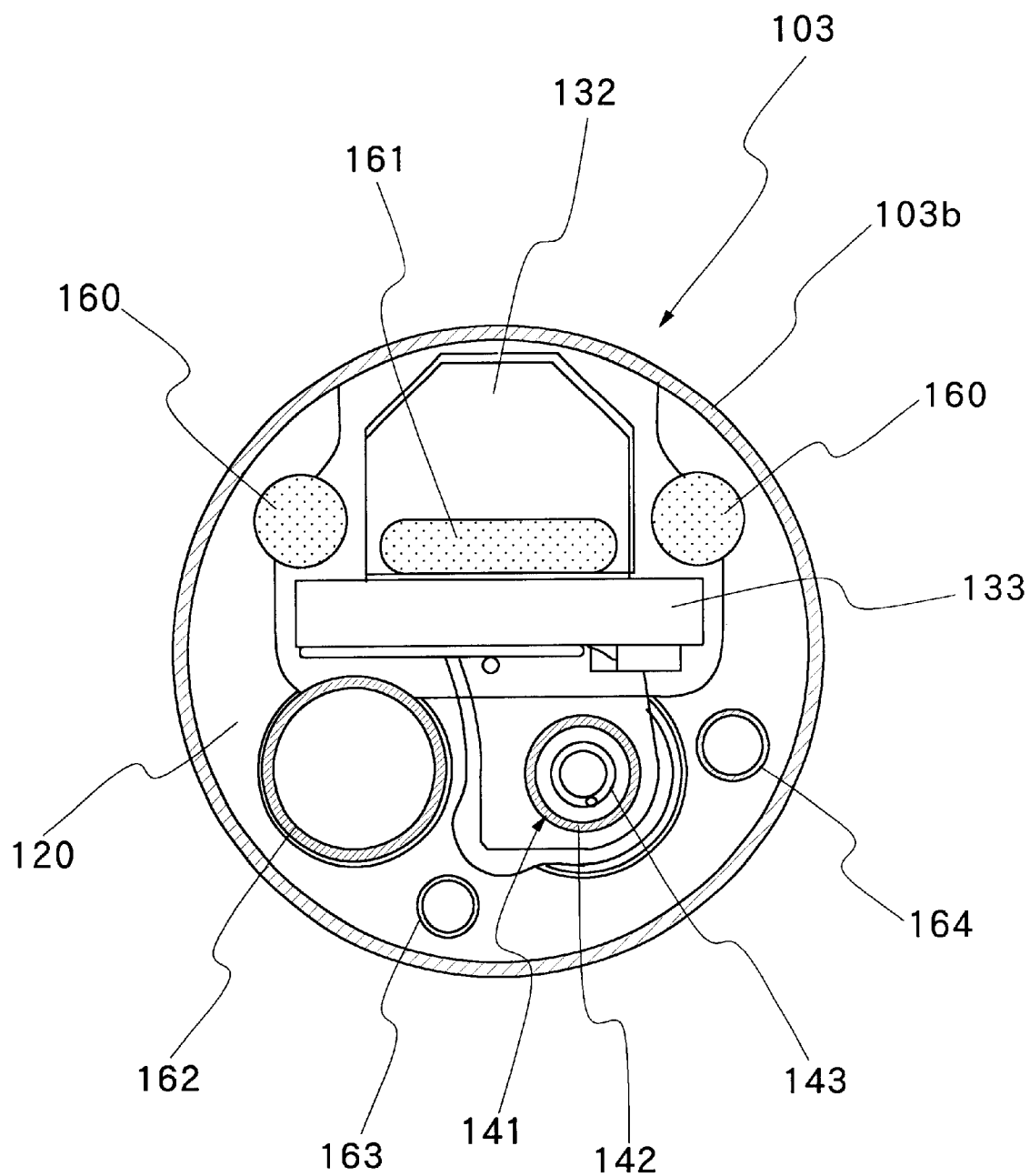
FIG. 14 is a schematic sectional view of a second embodiment of the present invention, taken substantially from the same position as in FIG. 10.
Figure 15:
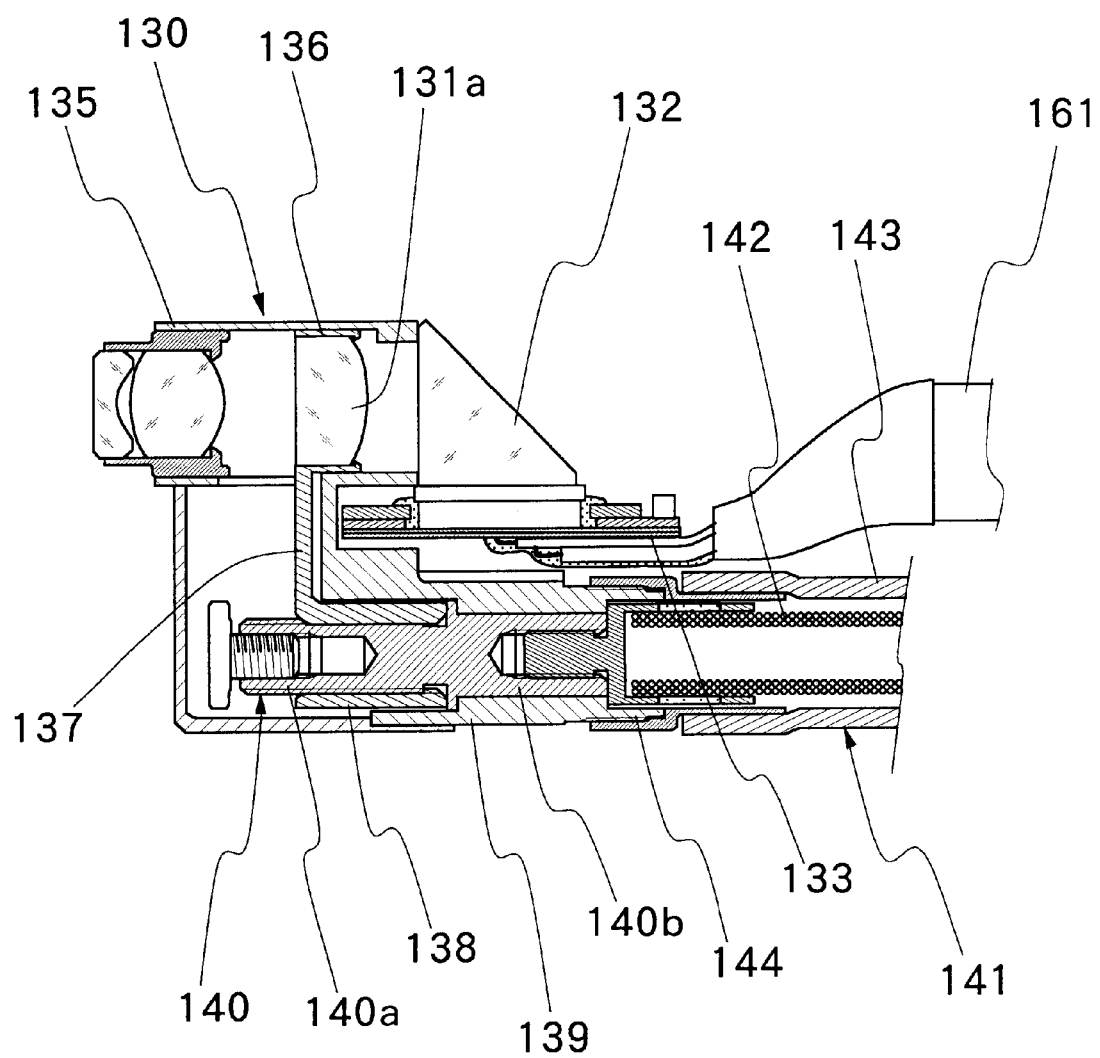
FIG. 15 is a fragmentary sectional view of another objective lens system and a movable lens drive mechanism therefore.

On the other hand, with regard to the image sensor means having a solid-state image sensor device mounted on a wiring substrate board, there has been a trend of using an image sensor device having a larger number of pixels and a broader image sensing area in order to obtain clear images of higher resolution. As shown in FIGS. 14 and 15, an image sensor assembly employing a large-size solid-state image sensor device of this sort can be incorporated into a fore end portion of an endoscopic insertion instrument of a small diameter, without necessitating to increase the outside diameter of the instrument to an objectionable degree.

More particularly, indicated at 103 in FIG. 14 is an endoscopic insertion instrument which is provided with a mounter block 120 in its rigid tip end section to mount thereon the respective internal component parts of the insertion instrument, which are passed through the angle section 3b in the manner as described above. Denoted at 133 is an image sensor assembly including a solid-state image sensor device 133a and a wiring substrate board 133b. The image sensor assembly 133 is located transversely of and substantially at the center position of the insertion instrument 103, having an image sensing surface disposed substantially parallel with the longitudinal axis of the insertion instrument 103. Located over the image sensor assembly 133 is a prism 132 which is joined with an objective lens assembly 130. Further, located under the prism 132 is a control cable 141 which has a flexible transmission shaft 143 fitted in a sleeve 142. A biopsy instrument channel 162, an air/water feed tube 163 and a jet feed tube 164 are located around the control cable 141. On the other hand, located over, the image sensor assembly 133 are light guides 160 and a signal cable 161 which is connected to the image sensor assembly 133.

As shown in FIG. 15, the control cable 141 functions to shift the position of a movable lens 131a of an objective lens group 131 in the direction of its optical axis. The fore end of its flexible transmission shaft 142 is connected to a screw rod 140. The screw rod 140 includes a screw portion 140a and a shaft portion 140b. In threaded engagement with the screw portion 140a is a nut portion 136b which is provided at the distal end of an arm member 136a of a movable lens frame 136. Fore end of a sleeve 142 of the control cable 141 is securely fixedly connected to a bearing member 144 through a connector member 144.

The arrangements just described make it possible to incorporate into a rigid tip end section of an endoscopic insertion instrument 103 an image sensor assembly with a large-size solid-state image sensor device having a broad image sensing area, without increasing the outside diameter of the insertion instrument 103 to a conspicuous degree.

Besides, the light guides 160 and signal cable 161 are located substantially in an upper half of the insertion instrument 103, while the control cable 141, biopsy instrument channel 162, air/water feed tube 163 and jet feed tube 164 are located in a lower half of the insertion instrument to utilize the internal space of the angle section 103b effectively. Therefore, breakage of fine fiber optics or bucking of tubular parts can be prevented even in a case where they are threaded in the insertion instrument at a high packing density. Further, there are little possibilities of the angle section 103b being twisted when flexed into a bent form. Furthermore, of the various parts which are threaded in the angle section 3b, relatively stiff or hard ones are all located in a lower half of the endoscopic insertion instrument. Therefore, the insertion instrument can be bent more easily in an upward direction than in other directions.

What is claimed is:

1. An endoscope with an objective lens drive mechanism, comprising:

an optical objective lens system incorporated into a rigid tip end section connected to a distal end of an elongated flexible body of an insertion instrument of said endoscope through an angularly bendable angle section and having a fixed lens mounted on a fixed lens frame provided within said rigid tip end section and a movable lens mounted on a movable lens frame for sliding movement in a direction toward and away from said fixed lens along inner surfaces of said fixed lens frame;

guide surfaces formed on an inner periphery of said fixed lens frame for guiding sliding movements of said movable lens frame in alignment with an optical axis of said objective lens system;

a rotational drive shaft for reciprocating said movable lens frame back and forth in the direction of the optical axis of said objective lens system;

an arm portion extended out from said movable lens frame in a radially outward direction substantially perpendicularly to said optical axis of said objective lens system for engagement with said rotational drive shaft;

a bearing member provided on said fixed lens frame and adapted to support said rotational drive shaft rotatably relative to said fixed lens frame but to block movements of said rotational drive shaft in an axial direction;

a control cable including a flexible transmission shaft connected between said rotational drive shaft and a rotational drive means to transmit rotation from said rotational drive means to said rotational drive shaft, and sheathed in a fixed sleeve having a fore end thereof securely fixed to said bearing member; and a plurality of stopper members provided on said rotational drive shaft to delimit forward and rearward stroke end positions of said movable lens frame.

2. An endoscope with an objective lens drive mechanism as defined in claim 1, wherein said optical objective lens system includes a prism securely bonded to said fixed lens frame thereby to turn a light path through 90 degrees toward a light receiving surface of a solid-state image sensor device which is located at the focus of said optical objective lens system substantially in parallel relation with a direction in which said control cable is extended.

3. An endoscope with an objective lens drive mechanism as defined in claim 2, wherein said solid-state image sensor device is located at a radially opposite side of said optical objective lens system within said rigid tip end section away from the direction of radial extension of said arm portion from said movable lens frame.

4. An endoscope with an objective lens drive mechanism as defined in claim 1, wherein said rotational drive shaft is in the form of a screw rod and provided with a stopper mechanism to be brought into and out of engagement with a nut portion provided at an outer end of said arm portion of said movable lens frame, said stopper mechanism being adapted to stop said movable lens frame at least at a preadjusted stroke end position on the side of a subject.

5. An endoscope with an objective lens drive mechanism as defined in claim 4, wherein said screw rod is provided with a second screw portion in a fore end portion thereof, and said stopper mechanism is provided with a stopper ring in threaded engagement with said second screw portion of said screw rod, wherein a position of said stopper ring on said second screw portion is adjustable to preset said nut portion in a stroke end position of said movable lens on the side of the subject.

6. An endoscope with an objective lens drive mechanism as defined in claim 5, wherein said stopper ring and said nut portion are provided with axially projecting sectoral land portions opposingly on confronting end faces, said sectoral land portions being so arranged as to be brought into abutting engagement with each other at a stroke end position of said movable lens.

7. An endoscope with an objective lens drive mechanism as defined in claim 4, wherein said stopper mechanism of said screw rod is adapted to stop said movable lens in both a front stroke end position on the side of the subject and a rear stroke end position on an imaging side of said objective lens system.

8. An endoscope with an objective lens drive mechanism as defined in claim 1, wherein said movable lens frame is provided with a sliding surface at two different positions on a circumference thereof for sliding contact with the inner surfaces of said fixed lens frame.

9. An endoscope with an objective lens drive mechanism as defined in claim 1, wherein said sleeve of said control cable is constituted by a tube which is treated with a lubricant to lessen frictions in sliding contact with said flexible transmission shaft.

10. An endoscope with an objective lens drive mechanism as defined in claim 9, wherein said sleeve is constituted by a silicon rubber tube impregnated with silicon oil.

11. An endoscope with an objective lens drive mechanism as defined in claim 1, wherein a nut portion is provided at an outer distal end of the arm portion extended out from said movable lens frame, said arm portion having a thickness substantially the same as an axial length of said movable lens frame.

12. An endoscope with an objective lens drive mechanism as defined in claim 11, wherein said arm portion is fitted in and blocked against rotational movements by an axial slot provided in said fixed lens frame.

13. An endoscope with an objective lens drive mechanism as defined in claim 11, wherein said nut portion is provided with an axial extension toward a proximal side of said arm portion thereby increasing a length of threaded engagement with said rotational drive shaft.

14. An endoscope with an objective lens drive mechanism as defined in claim 13, wherein said bearing member is provided with an open receptacle portion of a diameter larger than an outside diameter of said nut portion to receive said axial extension of said nut portion therein.

* * * * *